(12) United States Patent
Udaka et al.

(10) Patent No.: US 10,412,234 B2
(45) Date of Patent: Sep. 10, 2019

(54) DIAGNOSTIC DEVICE AND DIAGNOSTIC METHOD

(71) Applicant: FUJI XEROX CO., LTD., Tokyo (JP)

(72) Inventors: Tsutomu Udaka, Yokohama (JP); Tomoyuki Mitsuhashi, Yokohama (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

(21) Appl. No.: 15/958,467

(22) Filed: Apr. 20, 2018

(65) Prior Publication Data

US 2018/0249018 A1 Aug. 30, 2018

Related U.S. Application Data

(63) Continuation of application No. PCT/JP2016/063047, filed on Apr. 26, 2016.

(30) Foreign Application Priority Data

Dec. 24, 2015 (JP) .................... 2015-251583

(51) Int. Cl.
*H04N 1/00* (2006.01)
*G01H 17/00* (2006.01)
(Continued)

(52) U.S. Cl.
CPC ......... *H04N 1/00029* (2013.01); *G01H 17/00* (2013.01); *G01N 29/14* (2013.01);
(Continued)

(58) Field of Classification Search
CPC .................... H04N 1/00029; G01H 17/00
See application file for complete search history.

(56) References Cited

U.S. PATENT DOCUMENTS

| 8,051,379 B2* | 11/2011 | Iwata | G06K 15/007 |
| | | | 715/744 |
| 2002/0130784 A1* | 9/2002 | Suzuki | G05B 15/02 |
| | | | 340/635 |

(Continued)

FOREIGN PATENT DOCUMENTS

| JP | 5-101246 A | 4/1993 |
| JP | 7-282089 A | 10/1995 |
| JP | 2007-79263 A | 3/2007 |
| JP | 2008-290288 A | 12/2008 |

OTHER PUBLICATIONS

Search Report dated May 24, 2016, issued by the International Searching Authority in counterpart International Patent Application No. PCT/JP2016/063047 (PCT/ISA/210).

(Continued)

*Primary Examiner* — Ibrahim Siddo
(74) *Attorney, Agent, or Firm* — Sughrue Mion, PLLC

(57) ABSTRACT

A diagnostic device includes an acquisition unit that acquires sound information, and a display that displays a first analysis result obtained by a time-frequency analysis on the sound information and plural second analysis results obtained by a time-frequency analysis on sound information of an abnormal sound, and that displays the second analysis results in descending order of a possibility presumed to be a cause of the abnormal sound and displays treatment candidates on a screen for inputting a treatment situation of the abnormal sound, based on an order in which the second analysis results have been displayed.

19 Claims, 24 Drawing Sheets

(51) Int. Cl.
    *G01N 29/14*     (2006.01)
    *G01N 29/42*     (2006.01)
    *G06Q 10/00*     (2012.01)
    *G01N 29/24*     (2006.01)
    *G01N 29/46*     (2006.01)

(52) U.S. Cl.
    CPC ......... *G01N 29/2481* (2013.01); *G01N 29/42* (2013.01); *G01N 29/46* (2013.01); *G06Q 10/20* (2013.01); *H04N 1/00037* (2013.01); *H04N 1/00076* (2013.01)

(56) References Cited

U.S. PATENT DOCUMENTS

| | | | |
|---|---|---|---|
| 2004/0112136 A1* | 6/2004 | Terry | G01M 13/028 |
| | | | 73/572 |
| 2007/0070456 A1* | 3/2007 | Nishimura | B41J 29/393 |
| | | | 358/504 |
| 2013/0114100 A1* | 5/2013 | Torii | G06F 11/0733 |
| | | | 358/1.14 |
| 2016/0161468 A1* | 6/2016 | Keays | G01N 33/4972 |
| | | | 73/23.3 |

OTHER PUBLICATIONS

Written Opinion dated May 24, 2016, issued by the International Searching Authority in counterpart International Patent Application No. PCT/JP2016/063047 (PCT/ISA/237).

\* cited by examiner

FIG. 5

| WAVEFORM DATA OF FREQUENCY ANALYSIS RESULT | SOUND DATA OF ABNORMAL SOUND | CAUSE OF ABNORMAL SOUND | COPING METHOD |
|---|---|---|---|
| WAVEFORM DATA 1 | SOUND DATA 1 | ABRASION OF PHOTOSENSITIVE DRUM | REPLACEMENT OF PHOTOSENSITIVE DRUM |
| WAVEFORM DATA 2 | SOUND DATA 2 | GREASE DEFICIENCY OF SHEET CONVEYING DEVICE | GREASE APPLYING |
| ..... | ..... | ..... | ..... |
| WAVEFORM DATA 30 | SOUND DATA 30 | TROUBLE OF DRIVE SYSTEM MOTOR | REPLACEMENT OF DRIVE SYSTEM MOTOR |

MODEL NAME: ABC001
MODEL NAME: ABC002
MODEL NAME: ABC003

*FIG. 15*

EXAMPLE OF TREATMENT RESULT INPUT SCREEN

PLEASE SELECT A TREATMENT RESULT
○ FIXED   ○ NOT FIXED   ○ UNCLEAR
○ NOT REPRODUCED

PLEASE SELECT ALL OF TREATED CAUSE COMPONENTS
☐ PHOTOSENSITIVE DRUM
☐ TRANSFER BELT
☐ FIXING DEVICE
☐ OTHER

PLEASE SELECT ALL OF TREATED CONTENTS
☐ COMPONENT REPLACEMENT
☐ OIL FILLING/CLEANING
☐ TENSION ADJUSTMENT
☐ TONER CARTRIDGE STIRRING
☐ OTHER

[ OK ]  [ CANCEL ]

10

EXAMPLE OF TREATMENT RESULT INPUT

EXAMPLE OF TREATMENT RESULT INPUT SCREEN

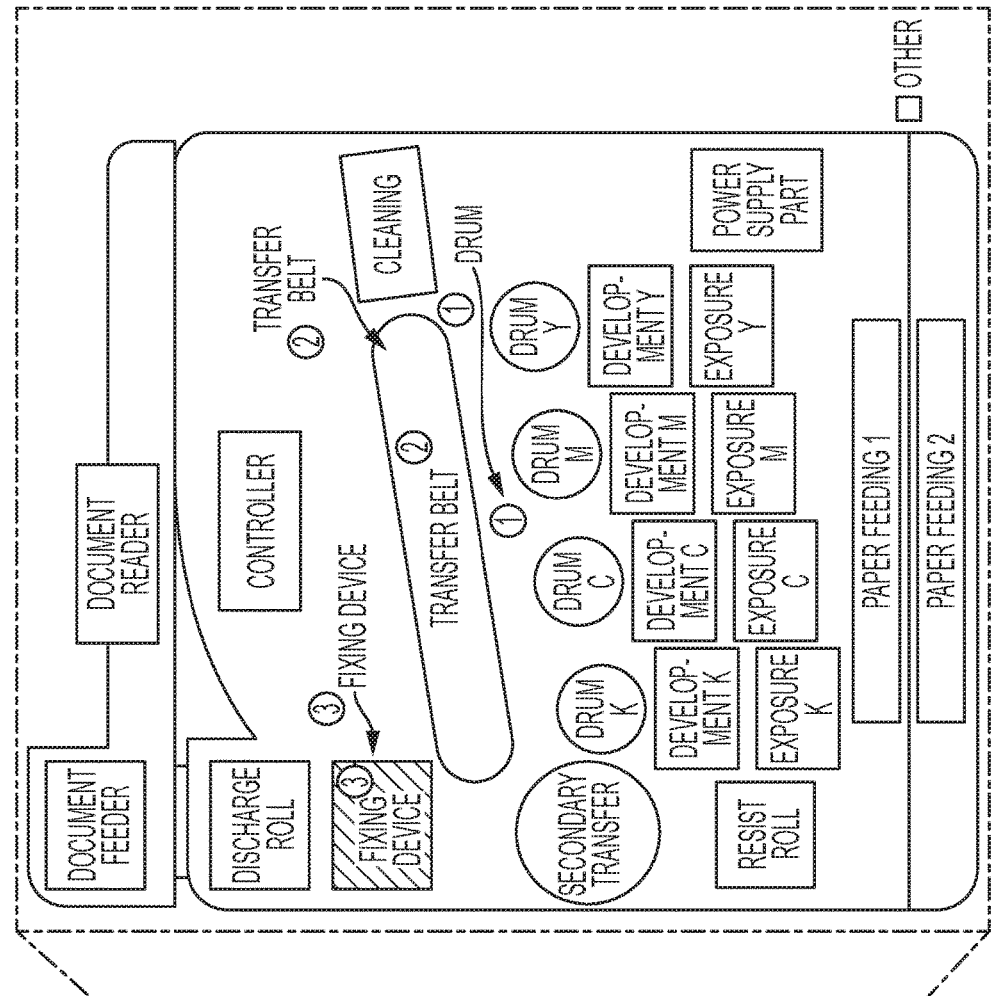
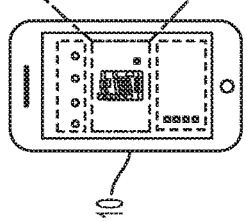
FIG. 18

FIG. 23

EXAMPLE OF TREATMENT RESULT INPUT SCREEN
(SERVICE ENGINEER A)

PLEASE SELECT A TREATMENT RESULT
◯ FIXED    ◯ NOT FIXED    ● UNCLEAR
◯ NOT REPRODUCED

PLEASE SELECT ALL OF TREATED CAUSE
COMPONENTS
☐ PHOTOSENSITIVE DRUM
☐ TRANSFER BELT
■ FIXING DEVICE
☐ OTHER

PLEASE SELECT ALL OF TREATED CONTENTS
■ COMPONENT REPLACEMENT
☐ OIL FILLING/CLEANING
☐ TENSION ADJUSTMENT
☐ TONER CARTRIDGE STIRRING
☐ OTHER

[ OK ]  [ CANCEL ]

EXAMPLE OF TREATMENT RESULT INPUT SCREEN
(SERVICE ENGINEER B)

PLEASE SELECT A TREATMENT RESULT
● FIXED   ○ NOT FIXED   ○ UNCLEAR
○ NOT REPRODUCED

PLEASE SELECT ALL OF TREATED CAUSE COMPONENTS
☐ PHOTOSENSITIVE DRUM
☐ TRANSFER BELT
☒ FIXING DEVICE
☐ OTHER

PLEASE SELECT ALL OF TREATED CONTENTS
☒ COMPONENT REPLACEMENT
☐ OIL FILLING/CLEANING
☐ TENSION ADJUSTMENT
☐ TONER CARTRIDGE STIRRING
☐ OTHER

[ OK ]  [ CANCEL ]

10B

DIAGNOSTIC DEVICE AND DIAGNOSTIC METHOD

CROSS-REFERENCE TO RELATED APPLICATIONS

This application is a continuation of International Application No. PCT/JP2016/063047 filed on Apr. 26, 2016 and is based on and claims priority under 35 USC 119 from Japanese patent Application No. 2015-251583 filed on Dec. 24, 2015.

BACKGROUND

Technical Field

The present invention relates to a diagnostic device, a diagnostic system, a diagnostic method, and a computer readable medium.

SUMMARY

According to an aspect of the invention, there is provided a diagnostic device including an acquisition unit that acquires sound information and a display that displays a first analysis result obtained by a time-frequency analysis on the sound information and plural second analysis results obtained by a time-frequency analysis on sound information of an abnormal sound, and that displays the second analysis results in descending order of a possibility presumed to be a cause of the abnormal sound and displays treatment candidates on a screen for inputting a treatment situation of the abnormal sound, based on an order in which the second analysis results have been displayed.

BRIEF DESCRIPTION OF THE DRAWINGS

Exemplary embodiment(s) of the present invention will be described in detail based on the following figures, wherein:

FIG. 5 depicts an example of information that is to be stored in a waveform data storage 53 of FIG. 4;

FIG. 7 depicts an example of a screen of the abnormal sound diagnostic device 10, which is displayed when inputting a variety of information such as a model name, a serial number, an operating state and the like;

FIG. 15 depicts an example of an input screen for inputting a treatment result (treatment situation) executed by a service engineer;

FIG. 18 is an enlarged view of a selection screen of the treated component candidates of FIG. 17;

FIG. 23 depicts an example of the input screen that is displayed when the service engineer A urged to input a treatment result inputs a treatment result;

FIG. 24 depicts an example of the input screen that is displayed the service engineer B urged to input a treatment result inputs a treatment result.

DESCRIPTION OF REFERENCE NUMERALS

Figure 1:
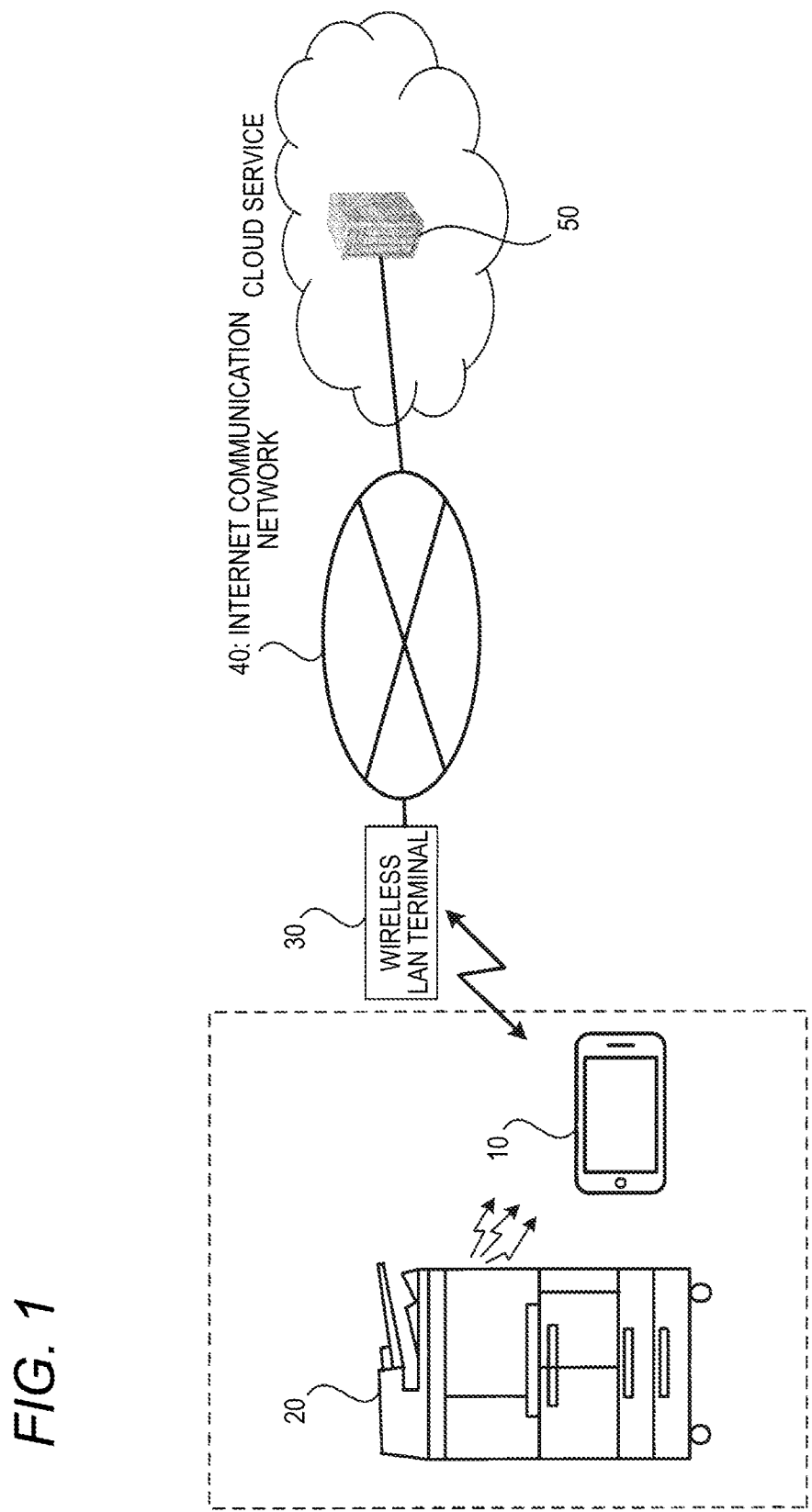
FIG. 1 is a system view depicting a configuration of an abnormal sound diagnostic system of an exemplary embodiment of the present invention.

10: abnormal sound diagnostic device
11: CPU
12: memory
13: storage device
14: wireless LAN interface (IF)
15: input device
16: display device
17: microphone
18: control bus
20: image forming apparatus
30: wireless LAN terminal
31: sound acquisition unit
32: frequency analysis unit
33: controller
34: sound data storage 35: display
36: communication unit
37: sound playback unit
40: Internet communication network
50: server apparatus
51: communication unit
52: controller
53: waveform data storage
61: frequency component of abnormal sound
62, 63: determination exclusion region
70: finger
80: selected region
90: popup display

DETAILED DESCRIPTION

An exemplary embodiment of the present invention will be described in detail with reference to the drawings.

FIG. 1 is a system view depicting a configuration of an abnormal sound diagnostic system of an exemplary embodiment of the present invention.

As shown in FIG. 1, the abnormal sound diagnostic system of the exemplary embodiment of the present invention includes a portable abnormal sound diagnostic device 10 such as a personal computer, a smart phone, a tablet terminal device and the like, and a server apparatus 50.

In the meantime, the present invention can be applied to any device, as the abnormal sound diagnostic device 10, inasmuch as the device can be connected to the server apparatus 50 via a communication network. In the exemplary embodiment, an example where the abnormal sound diagnostic device 10 is a tablet terminal device including a device such as a microphone capable of acquiring a sound signal and a touch panel by which a touch input can be performed is described.

The abnormal sound diagnostic device 10 is carried by a service engineer (maintenance personnel) who manages and repairs an image forming apparatus 20 such as a printer, which is used by an end user, for example. The abnormal sound diagnostic device 10 is used to acquire an abnormal sound signal generated in the image forming apparatus 20, to perform a frequency analysis on the acquired abnormal sound signal, and to display a frequency analysis result waveform of a past abnormal sound signal acquired from the server apparatus 50 and a frequency analysis result waveform of the acquired abnormal sound signal.

The abnormal sound diagnostic device 10 and the server apparatus 50 are connected to each other via a wireless LAN (Local Area Network) terminal 30 such as a Wi-Fi router and an Internet communication network 40 and are configured to transmit and receive information.

In the meantime, when the abnormal sound diagnostic device 10 is a portable phone device, a smart phone or the like, the abnormal sound diagnostic device 10 and the server apparatus 50 may be connected to each other via a portable phone network and configured to transmit and receive frequency analysis result waveform data.

In the abnormal sound diagnostic system of the exemplary embodiment, when an abnormal sound is generated in the image forming apparatus 20, which is a target electronic device provided at a place of the end user, the service engineer goes to the place of the image forming apparatus 20 with carrying the abnormal sound diagnostic device 10. The service engineer performs an abnormal sound diagnosis of recording the generated abnormal sound to acquire an abnormal sound signal by using the abnormal sound diagnostic device 10 and specifying a cause of the abnormal sound.

In the meantime, it is technically viable to provide the image forming apparatus 20 with a microphone and the like for a recording function and to record the abnormal sound by the recording function when the abnormal sound is generated. However, when the image forming apparatus 20 is provided in an office or the like of the end user, it is difficult to provide the image forming apparatus 20 with a sound recording function due to security reasons.

Figure 2:
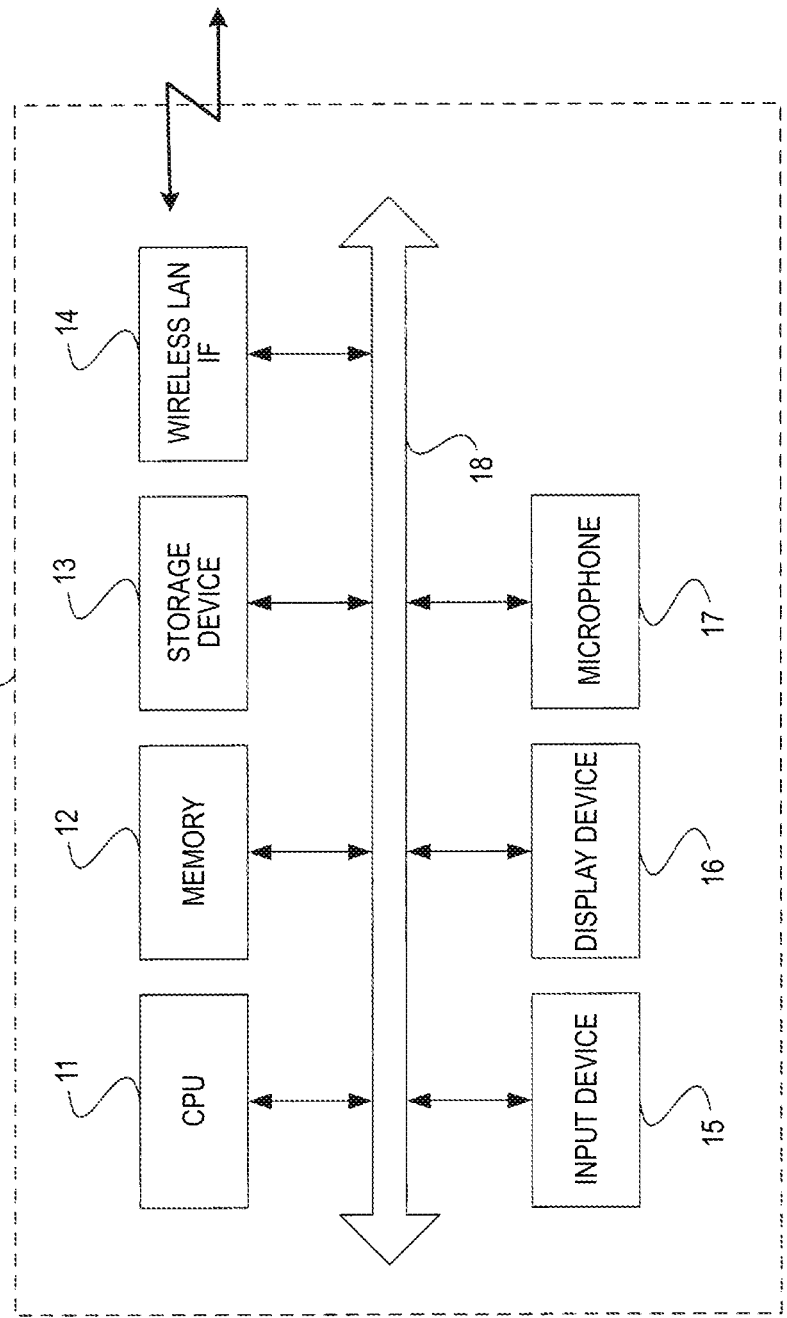
FIG. 2 is a block diagram depicting a hardware configuration of an abnormal sound diagnostic device 10 of the exemplary embodiment of the present invention.

FIG. 2 depicts a hardware configuration of the abnormal sound diagnostic device 10 of the abnormal sound diagnostic system of the exemplary embodiment. As shown in FIG. 2, the abnormal sound diagnostic device 10 includes a CPU 11, a memory 12 that temporarily stores data, a storage device 13 such as a flash memory, a wireless LAN interface (IF) 14 configured to transmit and receive data through wireless communication with the wireless LAN terminal 30, an input device 15 such as a touch sensor, a display device 16, and a microphone 17. The constitutional elements are connected to each other via a control bus 18.

The abnormal sound diagnostic device 10 of the exemplary embodiment is provided with a touch panel in which a touch sensor for detecting a touch position is provided as the input device 15 on the display device 16. A display and an input from a user are performed through the touch panel.

The CPU 11 is configured to execute predetermined processing based on a control program stored in the memory 12 or the storage device 13, thereby controlling an operation of the abnormal sound diagnostic device 10. In the meantime, the control program may be downloaded and provided to the CPU 11 through the Internet communication network 40 or portable phone network. Alternatively, the program may be provided to the CPU 11 with being stored in a storage medium such as a CD-ROM.

The control program is executed, so that the abnormal sound diagnostic device 10 of the exemplary embodiment performs operations as described later, thereby helping the service engineer to specify the cause of the abnormal sound.

Figure 3:
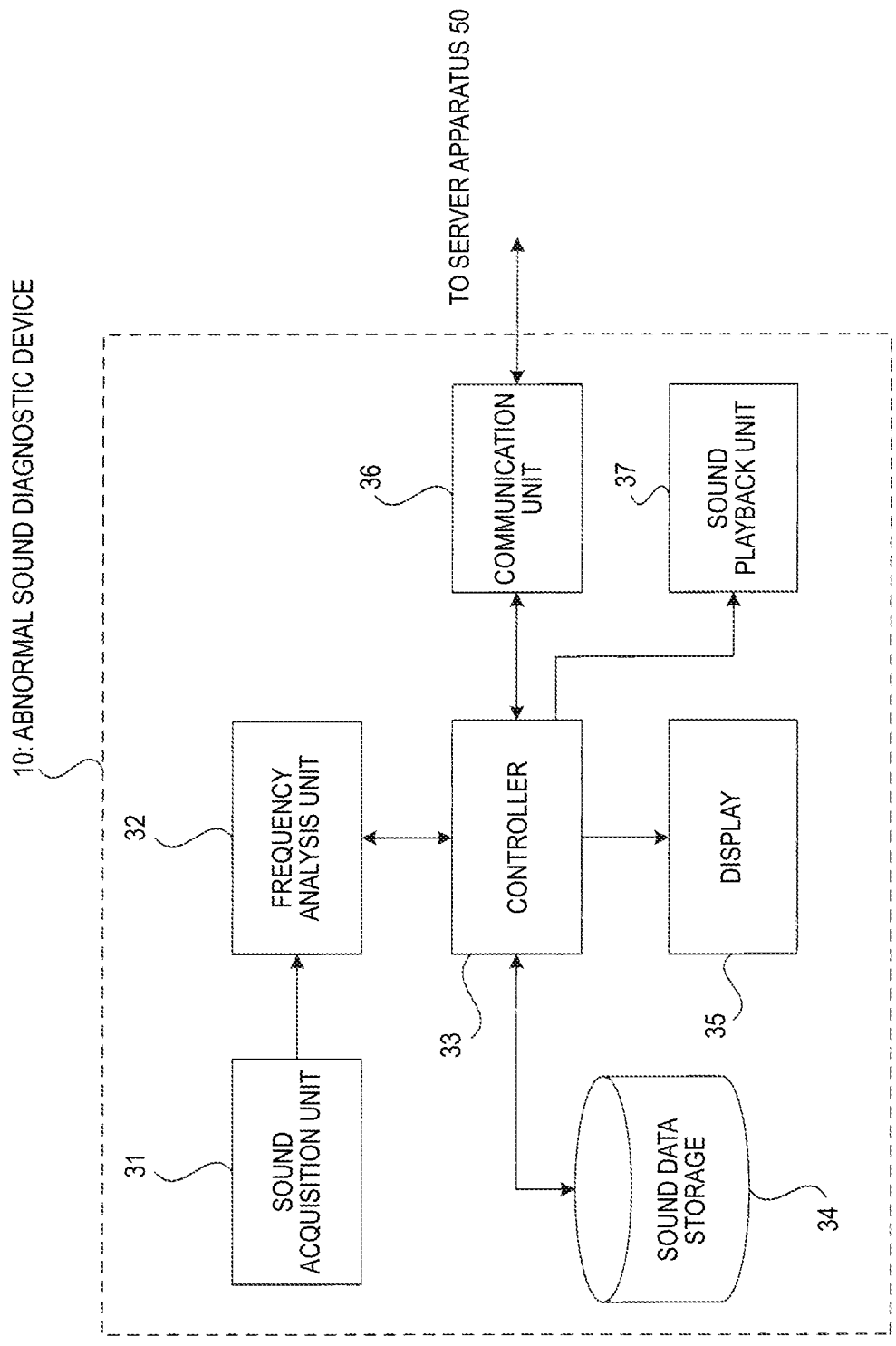
FIG. 3 is a block diagram depicting a functional configuration of the abnormal sound diagnostic device 10 of the exemplary embodiment of the present invention.

FIG. 3 is a block diagram depicting a functional configuration of the abnormal sound diagnostic device 10 that is implemented as the control program is executed.

As shown in FIG. 3, the abnormal sound diagnostic device 10 of the exemplary embodiment includes a sound acquisition unit 31, a frequency analysis unit 32, a controller 33, a sound data storage 34, a display 35, a communication unit 36, and a sound playback unit 37.

The display 35 is configured to display a variety of data under control of the controller 33. The communication unit 36 is configured to perform communication with the server apparatus 50, which is an external apparatus. The sound playback unit 37 is configured to play back recorded sound data and the like and to convert the data into a sound signal under control of the controller 33.

The sound acquisition unit 31 is configured to input therein the abnormal sound generated in the image forming apparatus 20, which is an analysis target apparatus, and to acquire a sound signal.

In the exemplary embodiment, the sound acquisition unit 31 is configured to input therein the abnormal sound generated in the image forming apparatus 20 and to acquire a sound signal. The sound signal is an example of the sound information.

The frequency analysis unit 32 is configured to perform a time-frequency analysis (time-dependent frequency analysis) on the sound signal acquired by the sound acquisition unit 31 and to generate frequency spectrum waveform (first analysis result) data indicative of a temporal change of a signal intensity distribution for each frequency of the acquired abnormal sound signal.

Specifically, the frequency analysis unit 32 is configured to perform STFT (Short time Fourier transform) on the sound signal acquired by the sound acquisition unit 31 and to generate frequency spectrum waveform data. The STFT will be described later.

The controller 33 is configured to store the frequency spectrum waveform data obtained by the frequency analysis unit 32 in the sound data storage 34, together with the sound data. The controller 33 is configured to display a frequency spectrum waveform obtained by a result of the STFT on the display 35, which is a touch panel.

Thereafter, when a user performs a touch operation of tracing a region, which is estimated as a signal component of the abnormal sound, of the frequency spectrum waveform displayed on the display 35 that is a touch panel by a finger, for example, the controller 33 receives a designation of the region, in which the signal component of the abnormal sound is included, of the displayed frequency spectrum waveform based on the user's touch operation.

Then, the controller 33 is configured to instruct the frequency analysis unit 32 to execute fast Fourier transform (1D-FFT (Fast Fourier Transform)) of performing a frequency analysis in a time-axis direction with respect to the frequency component of the region designated as the region, in which the signal component of the abnormal sound is included, of the frequency spectrum waveform data obtained by the frequency analysis unit 32. The frequency analysis unit 32 is configured to perform the fast Fourier transform in the time-axis direction with respect to the frequency component included in the instructed region.

Then, the controller 33 is configured to extract information of a period and a frequency of the abnormal sound from an analysis result of the fast Fourier transform in the frequency analysis unit 32.

In the meantime, even when the abnormal sound is not generated, a signal component of a usual operating sound is always included in a low-frequency region of a preset frequency or lower. For this reason, even when the region of the preset frequency or lower is designated as the region in which the signal component of the abnormal sound is included, the controller 33 may not receive the designation.

Also, the controller 33 is configured to transmit the obtained information of the period and the frequency of the abnormal sound to the server apparatus 50 via the communication unit 36, together with model information such as a model name and a serial number of the image forming apparatus 20 and operating state information indicative of an operating state of the image forming apparatus 20. The operating state information may specifically include information as to whether a color printing or a monochrome printing, whether a duplex printing or one-side printing, whether an operation mode is a scan mode, a print mode or a copy mode, and a type of a sheet to be used. In this way, the controller 33 is configured to transmit the information obtained from the frequency spectrum waveform data obtained by the frequency analysis unit 32 to the server apparatus 50 via the communication unit 36.

The server apparatus 50 is configured to store therein spectrum waveform data, which is obtained by performing a frequency analysis on a sound signal of an abnormal sound previously generated in an apparatus equivalent to the image forming apparatus 20, together with information of original sound data, an operating state of the apparatus upon acquisition of the sound data, a cause of the abnormal sound, a method of coping with the abnormal sound, and the like.

The server apparatus 50 is configured to search for a frequency spectrum waveform (second analysis result) data, which corresponds to the frequency spectrum waveform data obtained by the frequency analysis of the frequency analysis unit 32, from the information of the period and the frequency of the abnormal sound transmitted from the abnormal sound diagnostic device 10. The server apparatus 50 is configured to transmit the searched frequency spectrum waveform data to the abnormal sound diagnostic device 10, together with information of sound data and the like stored as abnormal sound sample waveform data.

As a result, the controller 33 is configured to receive the frequency spectrum waveform data, which corresponds to the frequency spectrum waveform data obtained by the frequency analysis of the frequency analysis unit 32, from the server apparatus 50 via the communication unit 36.

The controller 33 is configured to display, on the display 35, the frequency spectrum waveform obtained by performing the frequency analysis on the sound signal acquired by the sound acquisition unit 31 and the spectrum waveform received from the server apparatus 50 in parallel.

In the meantime, when there exists the plural frequency spectrum waveform data transmitted from the server apparatus 50, the controller 33 preferentially displays data, which is highly similar to the frequency spectrum waveform data obtained by the frequency analysis of the frequency analysis unit 32, of the plural frequency spectrum waveform data, on the display 35.

Therefore, the controller 33 is configured to display a frequency spectrum waveform obtained by performing the time-frequency analysis on the sound signal acquired by the sound acquisition unit 31 and to display the plural frequency spectrum waveforms received from the server apparatus 50 in order of presumed likelihood of being the cause of the abnormal sound.

The controller 33 is configured to display treated component candidates on a screen for inputting a treatment situation of the abnormal sound after the treatment for the abnormal sound has been completed, based on the order in which the plural frequency spectrum waveforms received from the server apparatus 50 has been displayed.

In the meantime, the display of the treated component candidates is not limited to a display of a list form. The controller 33 may be configured to display a pictorial view or an apparatus outer appearance image for receiving an input of a treated component, in which constitutional components are provided with priority orders based on the order in which the plural frequency spectrum waveforms received from the server apparatus 50 has been displayed, on the screen for inputting a treatment situation of the abnormal sound.

Also, the controller 33 is configured to display, on the screen for inputting a treatment situation of the abnormal sound, an option indicating that the abnormal sound has been eliminated, an option indicating that the abnormal sound has not been eliminated and an option indicating that whether the abnormal sound has been eliminated is unclear.

When there is a non-input item of input items of the treatment situation of the abnormal sound, the controller 33 may display information indicating that there is a non-input item.

Here, as the input items of the treatment situation, items of a treatment result, a treated component and a treatment content are provided.

In the meantime, a specific example of the input screen of the treatment situation will be described later.

Figure 4:
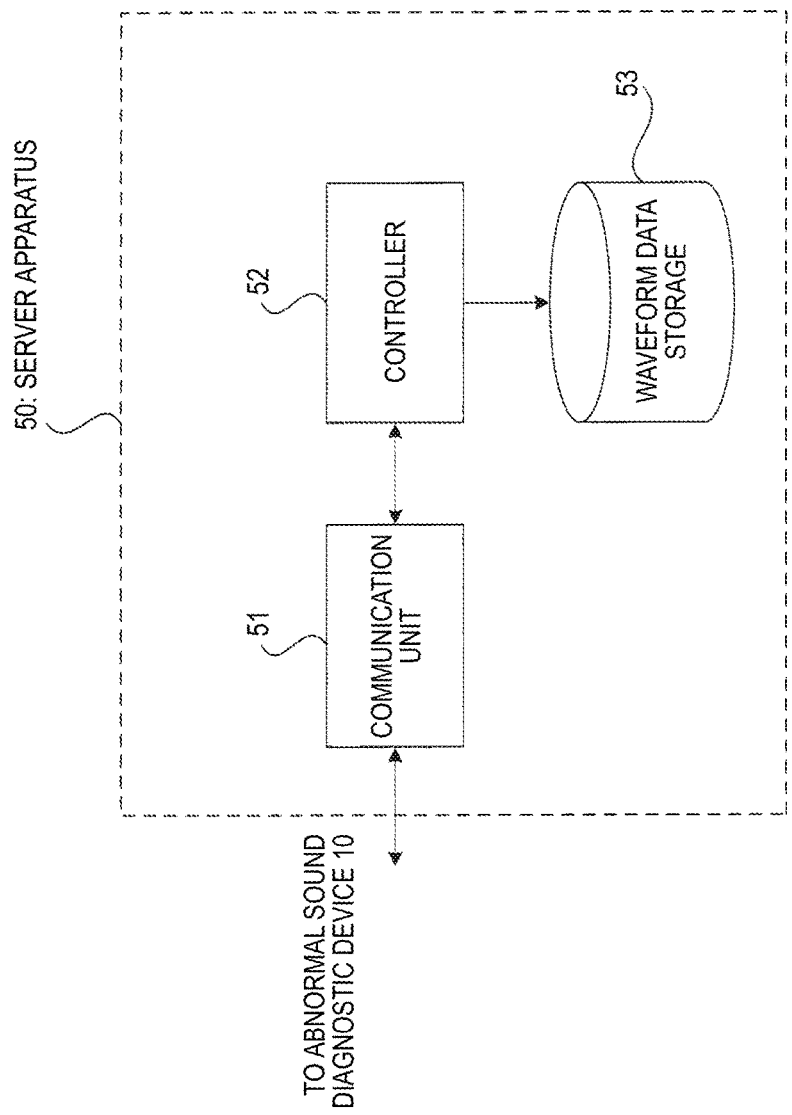
FIG. 4 is a block diagram depicting a functional configuration of a server apparatus 50 of the exemplary embodiment of the present invention.

FIG. 4 is a block diagram depicting a functional configuration of the server apparatus 50 in the abnormal sound analysis system of the exemplary embodiment.

As shown in FIG. 4, the server apparatus 50 of the exemplary embodiment includes a communication unit 51, a controller 52, and a waveform data storage 53.

The waveform data storage 53 is configured to store therein plural frequency spectrum waveform data, which is obtained by performing a frequency analysis on a sound signal of an abnormal sound previously generated in an apparatus equivalent to the image forming apparatus 20, which is an analysis target apparatus.

Specifically, as shown in FIG. 5, the waveform data storage 53 is configured to store therein information of frequency spectrum waveform data obtained by performing a time-frequency analysis on sound data of an abnormal sound acquired in advance, original sound data, a cause of the abnormal sound, a method of coping with the abnormal sound, and the like, for each model.

When the information of the period and the frequency of the abnormal sound is received from the abnormal sound diagnostic device 10, the controller 52 selects waveform data, which is similar to the frequency spectrum waveform data based on the abnormal sound acquired with the abnormal sound diagnostic device 10, from the plural frequency spectrum waveform data stored in the waveform data storage 53 based on the received information of the period and the frequency of the abnormal sound. Then, the controller 52 is configured to transmit the selected waveform data to the abnormal sound diagnostic device 10 via the communication unit 51.

Figure 6:
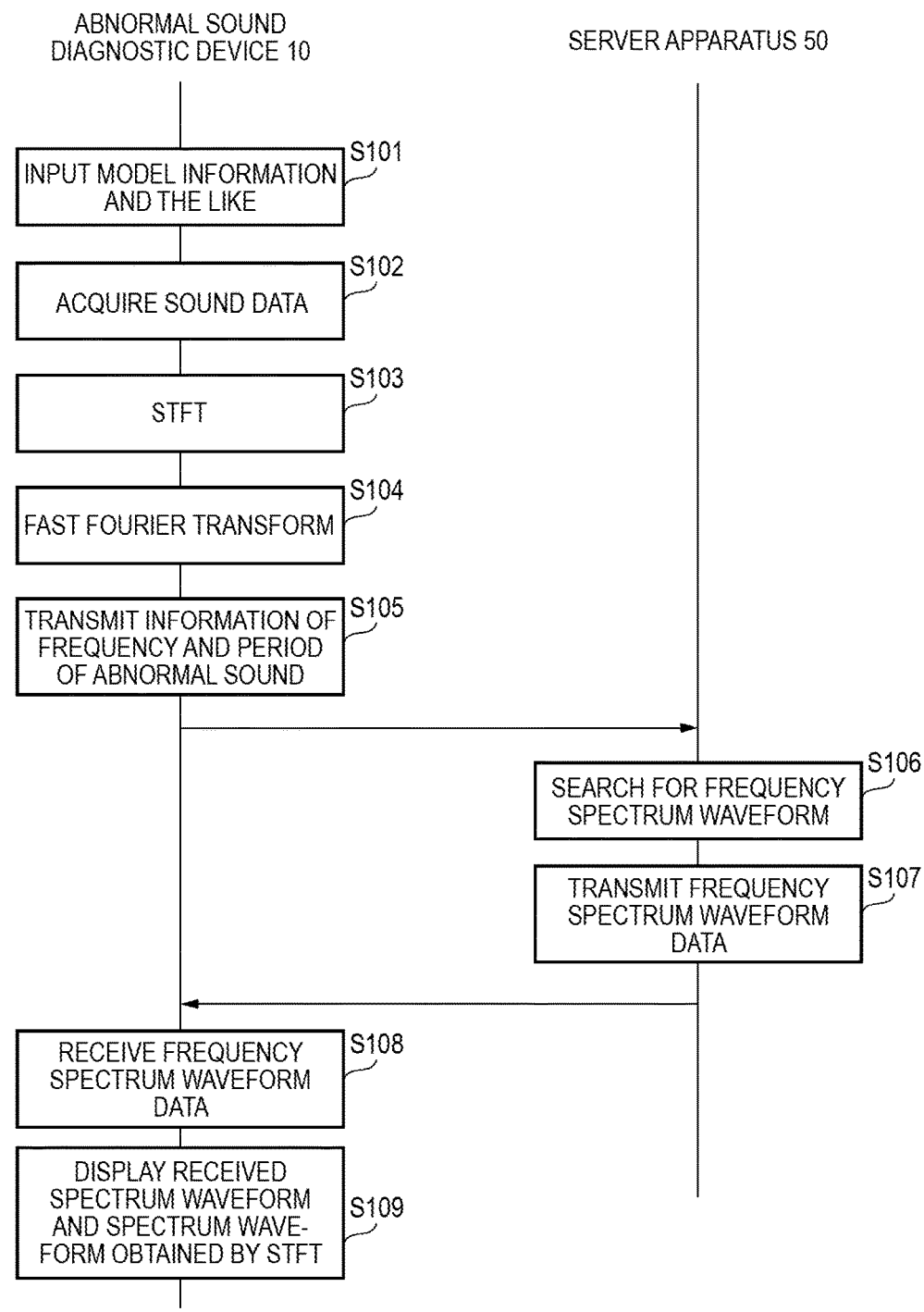
FIG. 6 is a sequence chart for illustrating an operation of the abnormal sound diagnostic system of the exemplary embodiment of the present invention.

Subsequently, an operation of the abnormal sound diagnostic system of the exemplary embodiment is described with reference to a sequence chart of FIG. 6.

Figure 7:
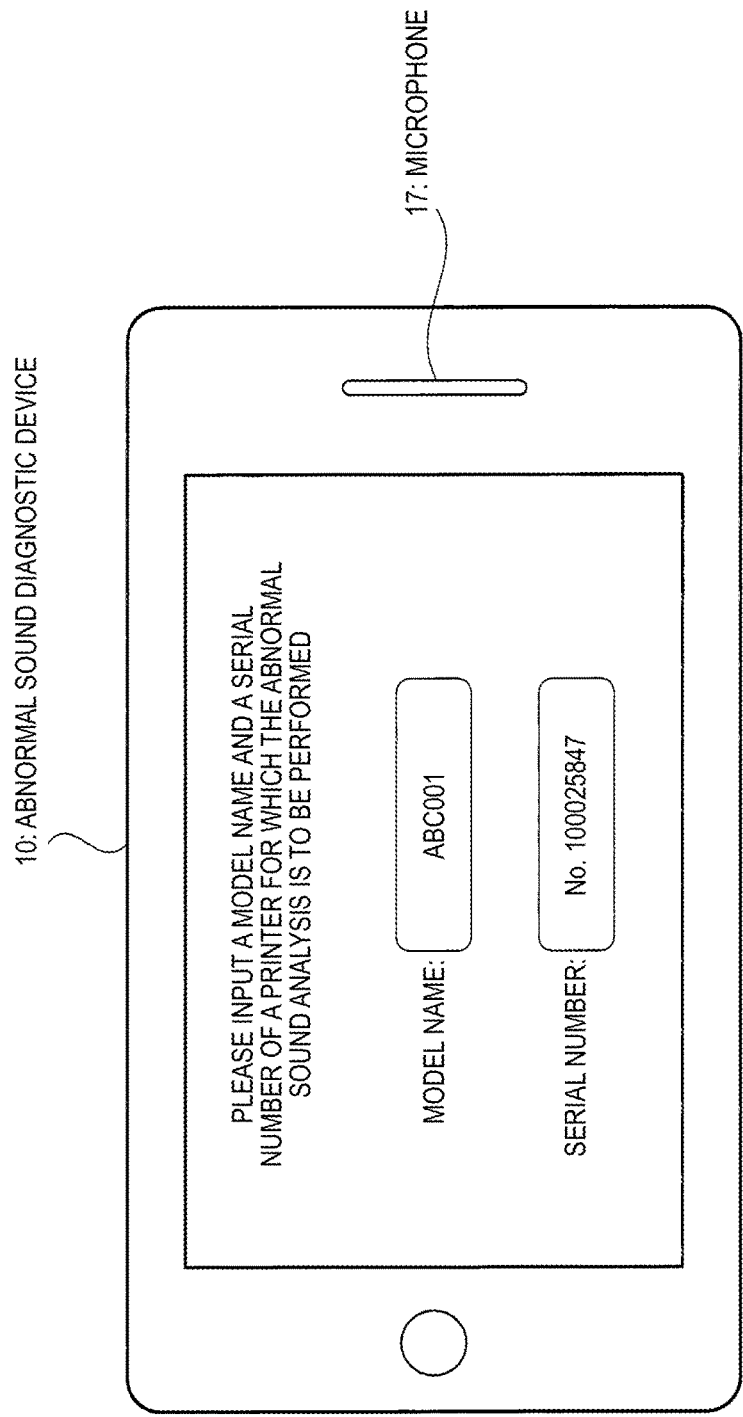

When diagnosing the abnormal sound so as to specify a cause of the abnormal sound with the abnormal sound diagnostic device 10, an image as shown in FIG. 7 is displayed, and various information such as a model name, a serial number, an operating state and the like is input (step S101).

The abnormal sound diagnostic device 10 sets an operation mode to a sound recording mode to record the abnormal sound by the microphone 17 close to a place of the image forming apparatus 20, at which the abnormal sound has been generated, thereby acquiring the sound data (step S102).

In the abnormal sound diagnostic device 10, the acquired sound data is subjected to the STFT by the frequency analysis unit 32, so that a frequency spectrum waveform indicative of a temporal change of a signal intensity distribution for each frequency is generated (step S103).

Figure 8:
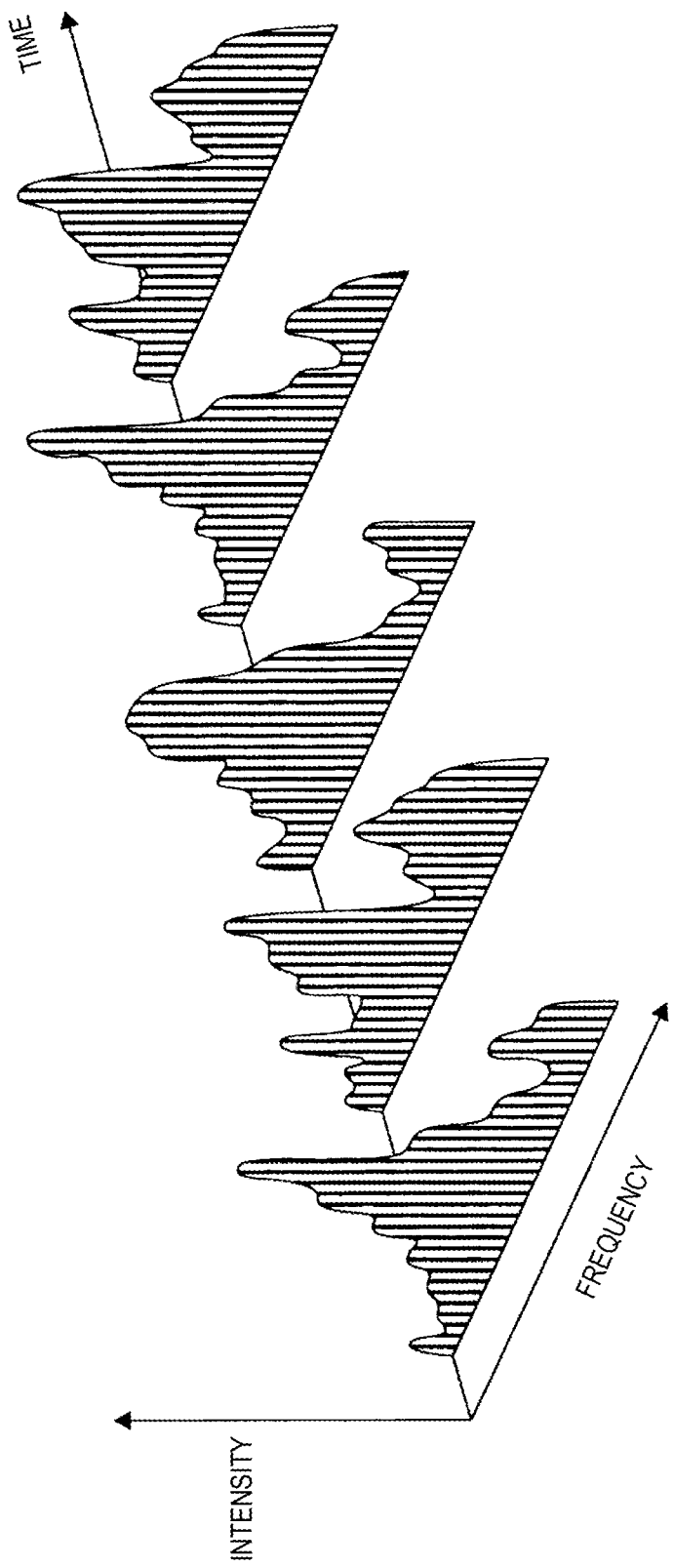
FIG. 8 illustrates a concept of an STFT.
Figure 9:
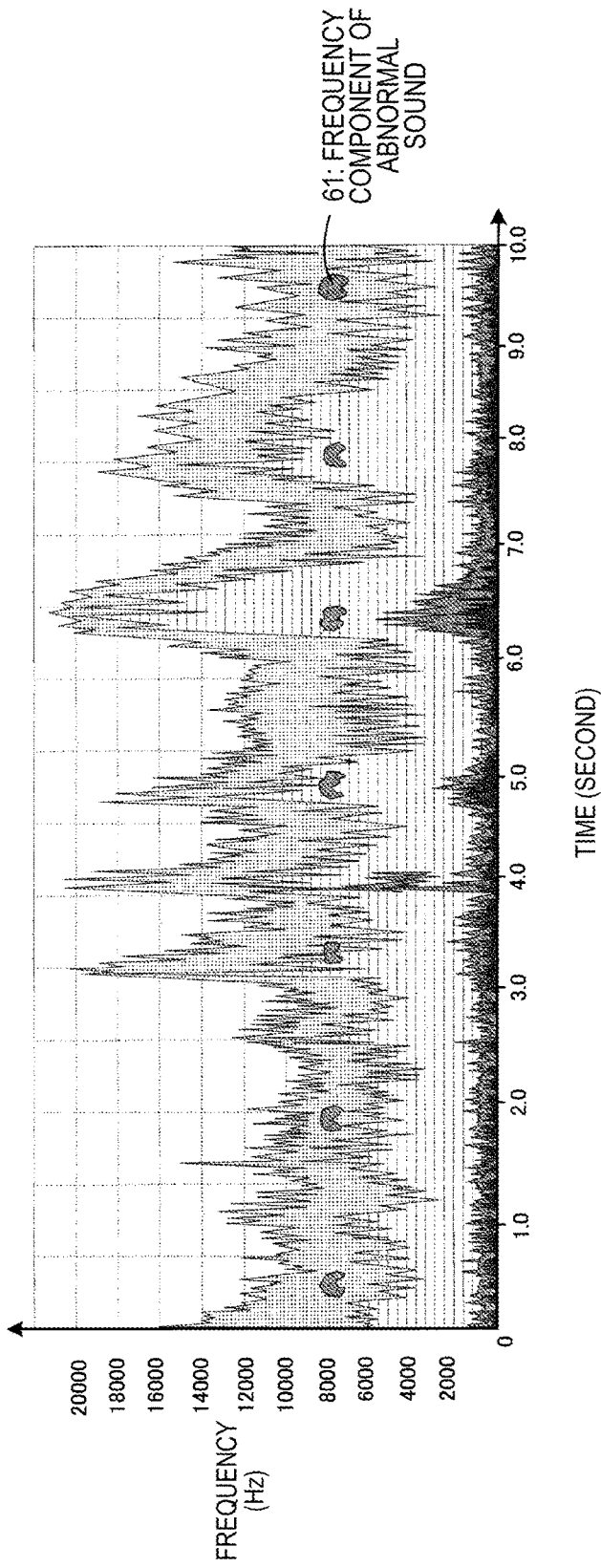
FIG. 9 depicts an example of an image of a frequency spectrum waveform based on an analysis result obtained by the STFT.

As shown in FIG. 8, the SIFT is processing of performing Fourier transform every short time to calculate a signal intensity for each frequency component in accordance with the temporal change. FIG. 9 depicts a waveform example where an analysis result obtained by the SIFT is shown by one frequency spectrum waveform image.

In the example of the frequency spectrum waveform shown in FIG. 9, a horizontal axis indicates time, a vertical axis indicates a frequency and an intensity for each frequency is expressed by a color. Meanwhile, in FIG. 9, a difference of colors is expressed by a hatching pattern. Also, FIG. 9 exemplifies a case where the intensity for each frequency is expressed by a color. However, the intensity may also be expressed by a gradation.

In the example of the frequency spectrum waveform shown in FIG. 9, it can be seen that a frequency component 61 of the abnormal sound is periodically generated at a specific frequency. Meanwhile, in the example of the frequency spectrum waveform shown in FIG. 9, a low-frequency component is a usual operating sound and is not the frequency component of the abnormal sound.

Figure 10:
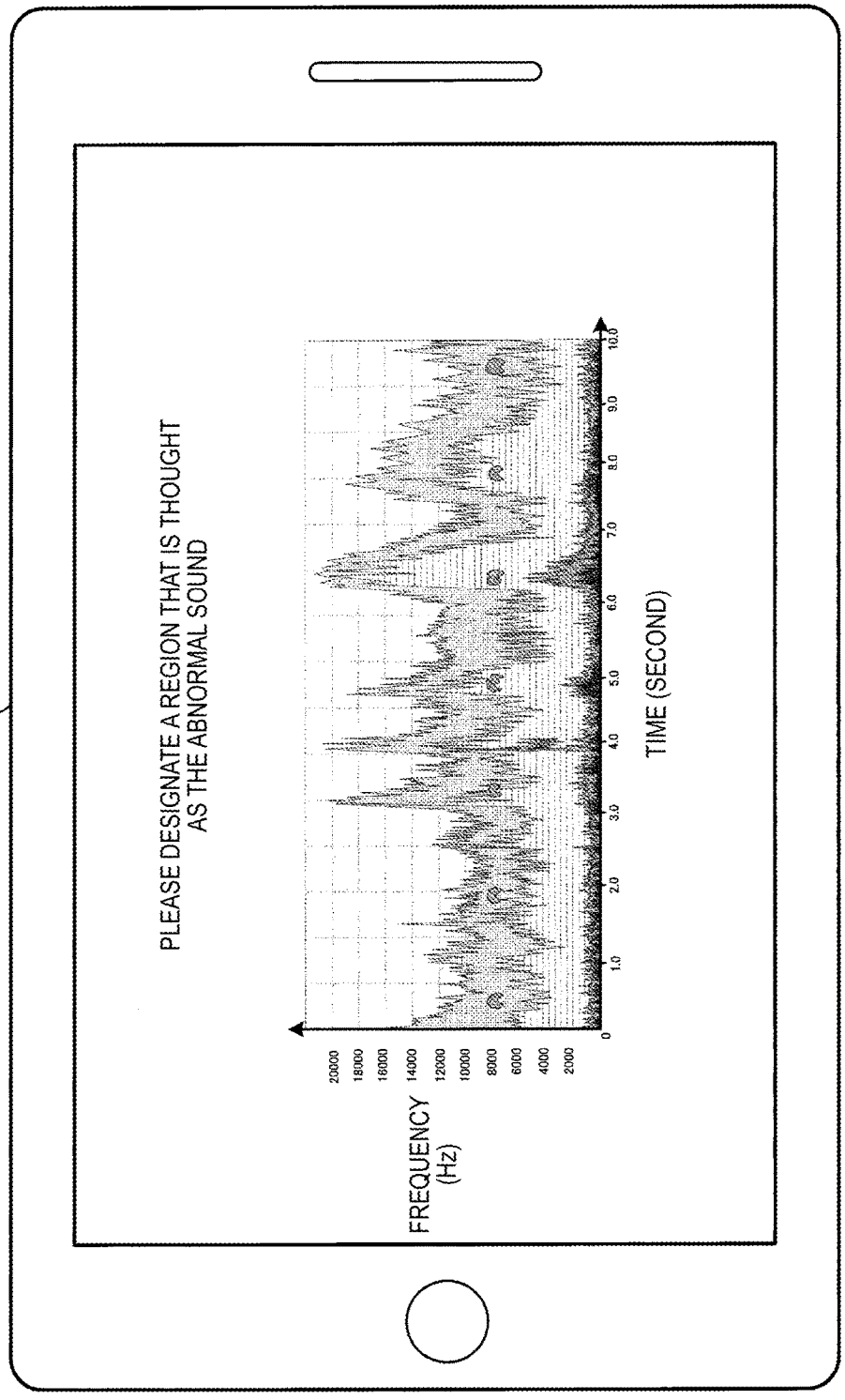
FIG. 10 depicts an example of a display for urging a user to designate a region estimated as an abnormal sound when presenting a frequency spectrum waveform to the user.

When the frequency spectrum waveform as shown in FIG. 9 is obtained, the controller 33 displays the frequency spectrum waveform on the display 35. Then, as shown in FIG. 10, the controller 33 presents a display for urging the user to designate a region, which is estimated as the abnormal sound, of the displayed frequency spectrum waveform. In the example of FIG. 10, it can be seen that the characters "Please designate a region that is thought as the abnormal sound" are displayed, so that the user is urged to designate a region that is estimated as the abnormal sound.

By referring to the above display, the user presented with the frequency spectrum waveform specifies the frequency component 61 of the abnormal sound, for example, operates the touch panel to select a region in which the frequency component 61 of the abnormal sound is included.

Figure 11:
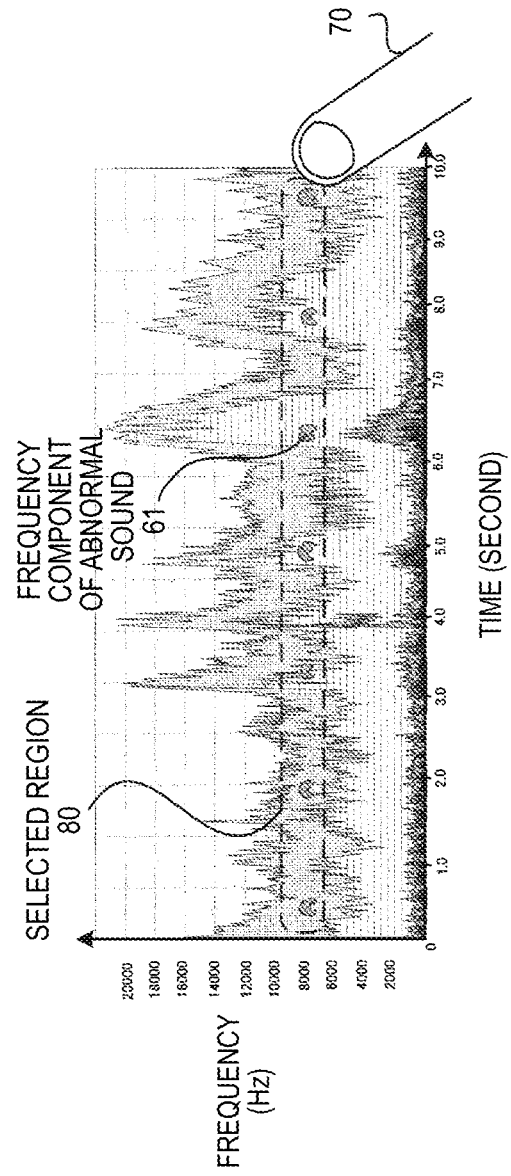
FIG. 11 depicts an example of a selected region 80 selected by the user in the image example of the frequency spectrum waveform shown in FIG. 10.

FIG. 11 depicts an example of a selected region 80 selected in this way by the user. In the example of FIG. 11, it can be seen that the user operates the touch panel with a finger 70 to designate a rectangular region including plural frequency components 61 of the abnormal sound, as the selected region 80.

Figure 12:
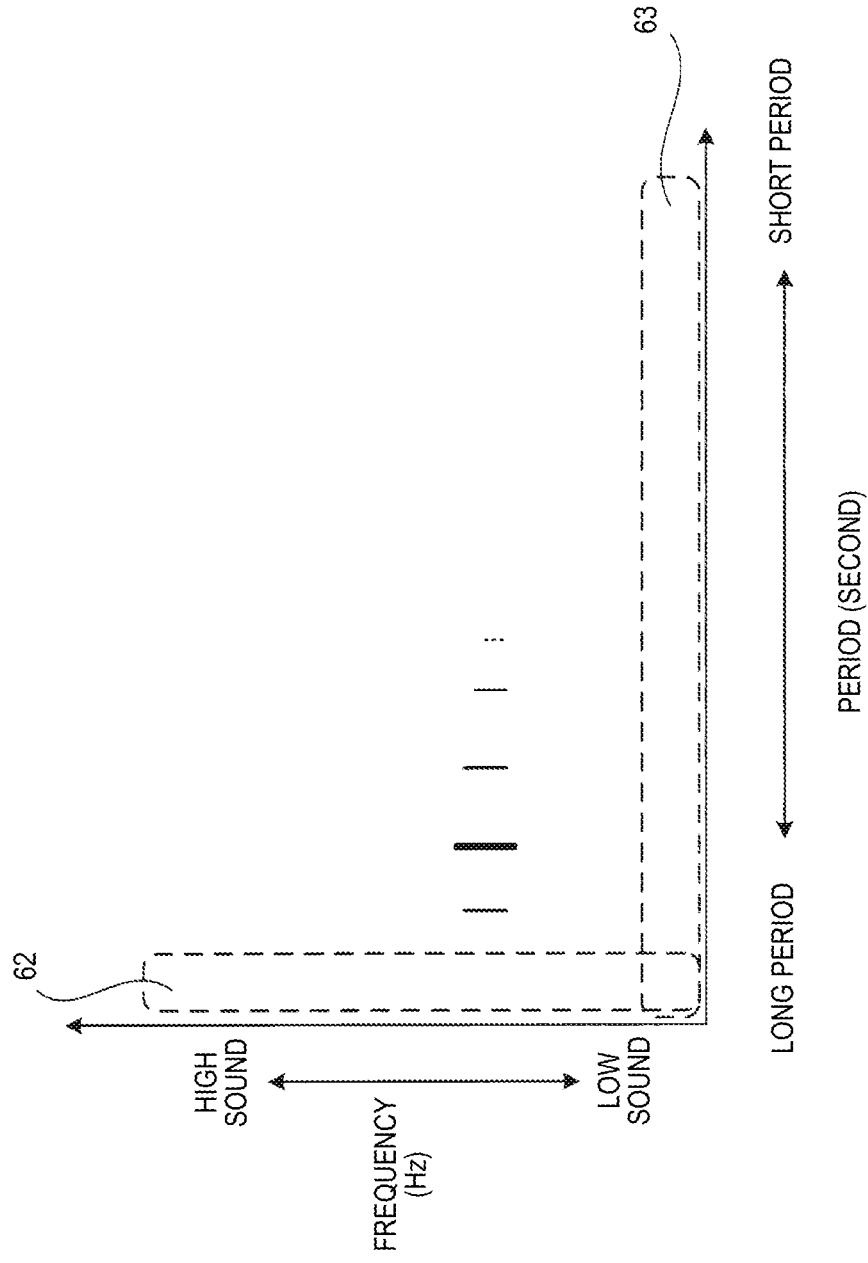
FIG. 12 depicts an analysis result example of fast Fourier transform.

When the selected region 80 is designated in this way, the fast Fourier transform (1D-FFT) is executed for the frequency components included in the selected region 80 by the frequency analysis unit 32 (step S104). FIG. 12 depicts an analysis result example of the fast Fourier transform executed in this way.

In FIG. 12, the period and the frequency of the signal of the frequency component for which the fast Fourier transform has been performed are detected to specify the period and frequency of the abnormal sound. In the meantime, since the abnormal sound includes an overtone component and the like, plural periods may be detected. However, a period in which the signal intensity is strongest is detected as the period of the abnormal sound.

Also, a signal component of a long period equal to or longer than a predetermined period is considered as a usual operating sound or a noise of an irregular period. Therefore, a region including the signal component of the long period is set as the determination exclusion region 62. An analysis result in the determination exclusion region 62 is ignored.

Also, since a low-frequency signal component of a predetermined frequency or lower is not also distinguished from a usual operating sound, a region including the low-frequency signal component is set as a determination exclusion region 63. An analysis result in the determination exclusion region 63 is ignored.

The abnormal sound diagnostic device 10 transmits the information of the frequency and the period of the abnormal sound obtained by the analysis result of the fast Fourier transform to the server apparatus 50, together with the model information and the information of the operating state (step S105). For example, the information that a frequency of the abnormal sound is 4 kHz and a period of the abnormal sound is 2.0 seconds is transmitted to the server apparatus 50.

Then, the server apparatus 50 searches the waveform data storage 53 based on the received information, thereby extracting the frequency spectrum waveform data corresponding to the received information (step S106).

Then, the server apparatus 50 transmits the extracted frequency spectrum waveform data to the abnormal sound diagnostic device 10, together with the information of the original sound data, the cause of the abnormal sound, the coping method thereof and the like (step S107).

The abnormal sound diagnostic device 10 receives the frequency spectrum waveform data transmitted from the server apparatus 50 (step S108). Then, the controller 33 of the abnormal sound diagnostic device 10 displays, on the display 35, the received frequency spectrum waveform and the frequency spectrum waveform obtained by the STFT (step S109).

Figure 13:
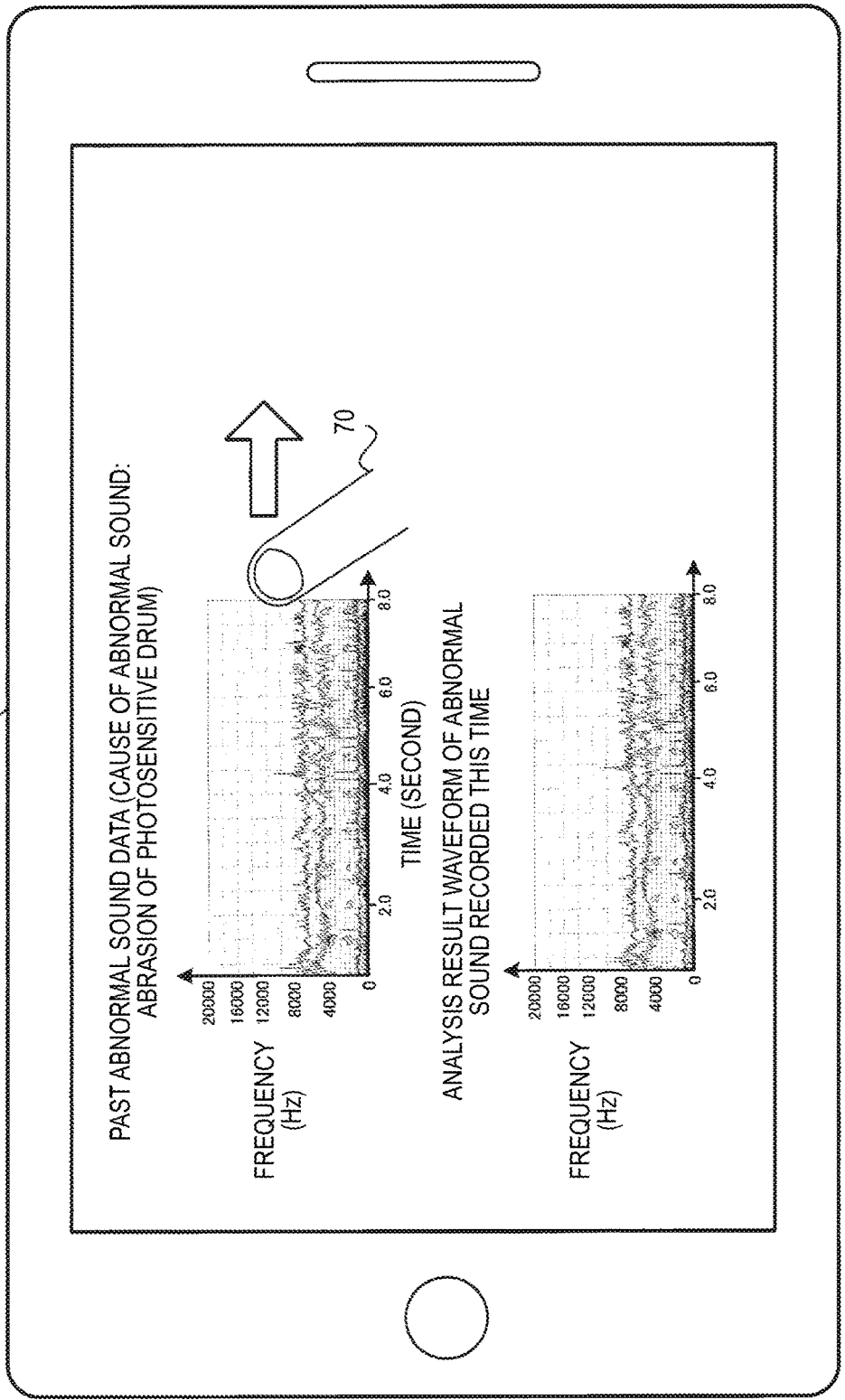
FIG. 13 depicts a screen example of the abnormal sound diagnostic device 10 in which two frequency spectrum waveforms are displayed.

FIG. 13 depicts a screen example of the abnormal sound diagnostic device 10, in which the two frequency spectrum waveforms are displayed in this way.

In the screen example of FIG. 13, it can be seen that the frequency spectrum waveform obtained by the STFT in the frequency analysis unit 32 is displayed as "the analysis result waveform of the abnormal sound recorded this time" and the frequency spectrum waveform transmitted from the server apparatus 50 is displayed as "the past abnormal sound data" together with the cause of the abnormal sound "abrasion of the photosensitive drum".

The service engineer who intends to perform the abnormal sound diagnosis compares the two frequency spectrum waveforms and determines whether the abnormal sound components in the waveforms are similar, thereby specifying the cause of the abnormal sound.

Figure 14:
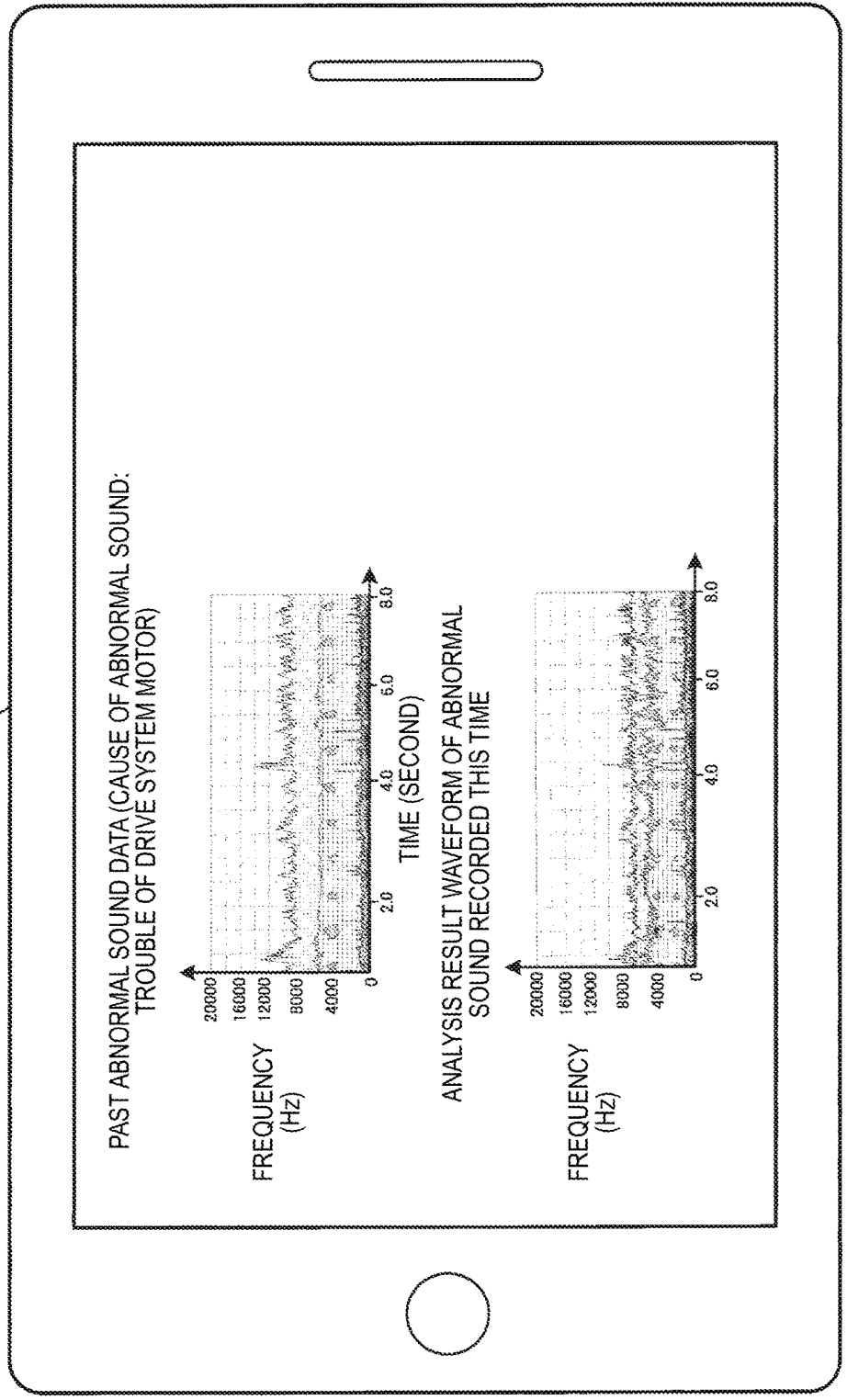
FIG. 14 depicts an image example where a separate frequency spectrum waveform having a different abnormal sound cause is displayed with respect to the screen example shown in FIG. 13.

Also, when plural frequency spectrum waveforms is transmitted from the server apparatus 50, the user traces an image of the frequency spectrum waveform displayed as "the past abnormal sound data" in the horizontal direction by a touch operation, so that a separate frequency spectrum waveform is displayed, as shown in FIG. 14.

FIG. 14 depicts an image example where the frequency spectrum waveform of the abnormal sound is displayed when the cause of the abnormal sound is "a trouble of the drive system motor".

Like this, when the plural frequency spectrum waveforms are transmitted, the service engineer determines to which frequency spectrum waveform the frequency spectrum waveform of the abnormal sound acquired this time is more similar, thereby specifying the cause of the abnormal sound. In the meantime, when specifying the cause of the abnormal sound, the service engineer hears and compares the abnormal sound acquired this time and the sound corresponding to the frequency spectrum waveform transmitted from the server apparatus 50 by playing back the original sound data with the sound playback unit 37, in addition to the comparison of the shapes of the frequency spectrum waveforms, the period and the frequency of the abnormal sound component, and the like, and then specifies the cause of the abnormal sound.

When the service engineer having specified the cause of the abnormal sound executes a treatment such as component replacement, component adjustment and the like, the service engineer reports a treatment situation from a treatment result (treatment situation) input screen as shown in FIG. 15.

As shown in FIG. 15, the reporting of the treatment situation includes items of a treatment result, a component for which the treatment has been executed (treated component), and an executed treatment content.

First, as shown in FIG. 15, as the option of the treatment result, four options of "Fixed", "Not fixed", "Unclear" and "Not Reproduced" are provided. The option "Fixed" is an option that is to be selected when the abnormal sound has been eliminated by executing a treatment for the abnormal sound cause. Also, the option "Not Fixed" is an option that is to be selected when the abnormal sound has not been eliminated even though a treatment for the abnormal sound cause has been executed.

Also, the option "Unclear" is an option that is to be selected when whether the abnormal sound has been eliminated is unclear. The reason to provide the options is that when a service engineer having specified the cause of the abnormal sound by the analysis on the cause of the abnormal and a service engineer having actually executed the treatment for the abnormal sound are different, the service engineer having specified the cause of the abnormal sound may not perceive whether the abnormal sound has been eliminated as a result of the treatment.

That is, a case is assumed in which when the service engineer having specified the cause of the abnormal sound has specified the cause of the abnormal sound but does not have a component for replacement, another service engineer may get the component at a later date and replace a component.

Here, if only the options "Fixed" and "Not Fixed" are provided, the service engineer having simply specified the cause of the abnormal sound may arbitrarily predict a treatment result and incorrectly select and input any one option, even though the service engineer does not know the treatment result.

The option "Unclear" is provided, so that an input of the incorrect result is prevented.

Also, the option "Not Reproduced" is an option that is to be selected when it is not possible to confirm the abnormal sound because the abnormal sound has not been generated even though the service engineer has operated the image forming apparatus 20.

Also, in the screen example of FIG. 15, as the option of the component for which the treatment has been executed (treated component), component names corresponding to abnormal sound cause components of the frequency spectrum waveforms transmitted from the server apparatus 50 are displayed as treated component candidates in a list form, in order corresponding to an order in which the frequency spectrum waveforms transmitted from the server apparatus 50 have been displayed.

Here, the order corresponding to the order in which the frequency spectrum waveforms transmitted from the server apparatus 50 have been displayed is a following order, for example. That is, as shown in FIGS. 13 and 14, when "abrasion of the photosensitive drum" is estimated as the most likely cause of the abnormal sound and then "trouble of the drive system motor" is estimated as the likely cause of the abnormal sound, the order is an order in which "photosensitive drum" is displayed as a first component of the treated component candidates and "drive system motor" is displayed as a next component of the treated component candidates.

Also, in the screen example of FIG. 15, the option "other" is also displayed together with the component names corresponding to the abnormal sound cause components of the frequency spectrum waveforms transmitted from the server apparatus 50.

That is, when the treatment such as replacement and cleaning has been executed for a component except the components displayed as the treated component candidates, the option "other" can be selected.

Also, in the screen of FIG. 15, as the option of the treated content, options of "component replacement", "oil filling/cleaning" and "tension adjustment" are displayed. Also in the option of the treatment content, when the treatment except the displayed treatment content candidates has been executed, the option "other" can be selected.

Figure 16:
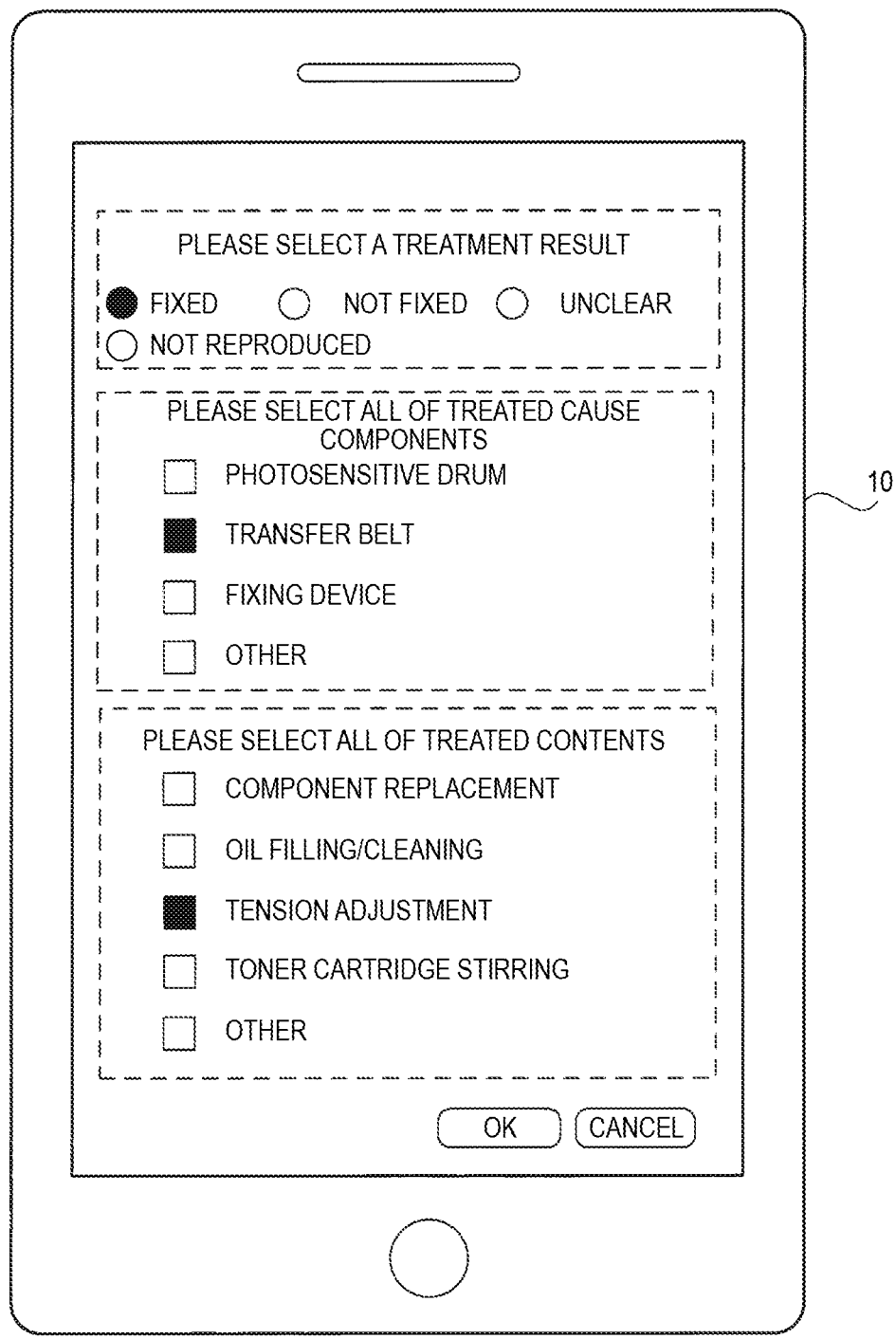
FIG. 16 depicts an example of a screen that is displayed when the treatment situation is actually input on the treatment result input screen example of FIG. 15.

FIG. 16 depicts a screen example that is displayed when the treatment situation is actually input on the treatment result input screen example as shown in FIG. 15.

In the input screen example of FIG. 16, "Fixed" is selected as the treatment result, "Transfer belt" is selected as the treated component, and "Tension adjustment" is selected as the treatment content.

When the input as described above is made, an input result is transmitted from the abnormal sound diagnostic device 10 to the server apparatus 50. Thereby, it is possible to perceive that the treatment content this time is tension adjustment of the transfer belt and the abnormal sound has been resultantly eliminated. For this reason, it is possible to perform processing of registering the sound data and the frequency spectrum waveform acquired this time, as a waveform example where the abnormal sound cause is "transfer belt" and the coping method is "tension adjustment", for example.

Figure 17:
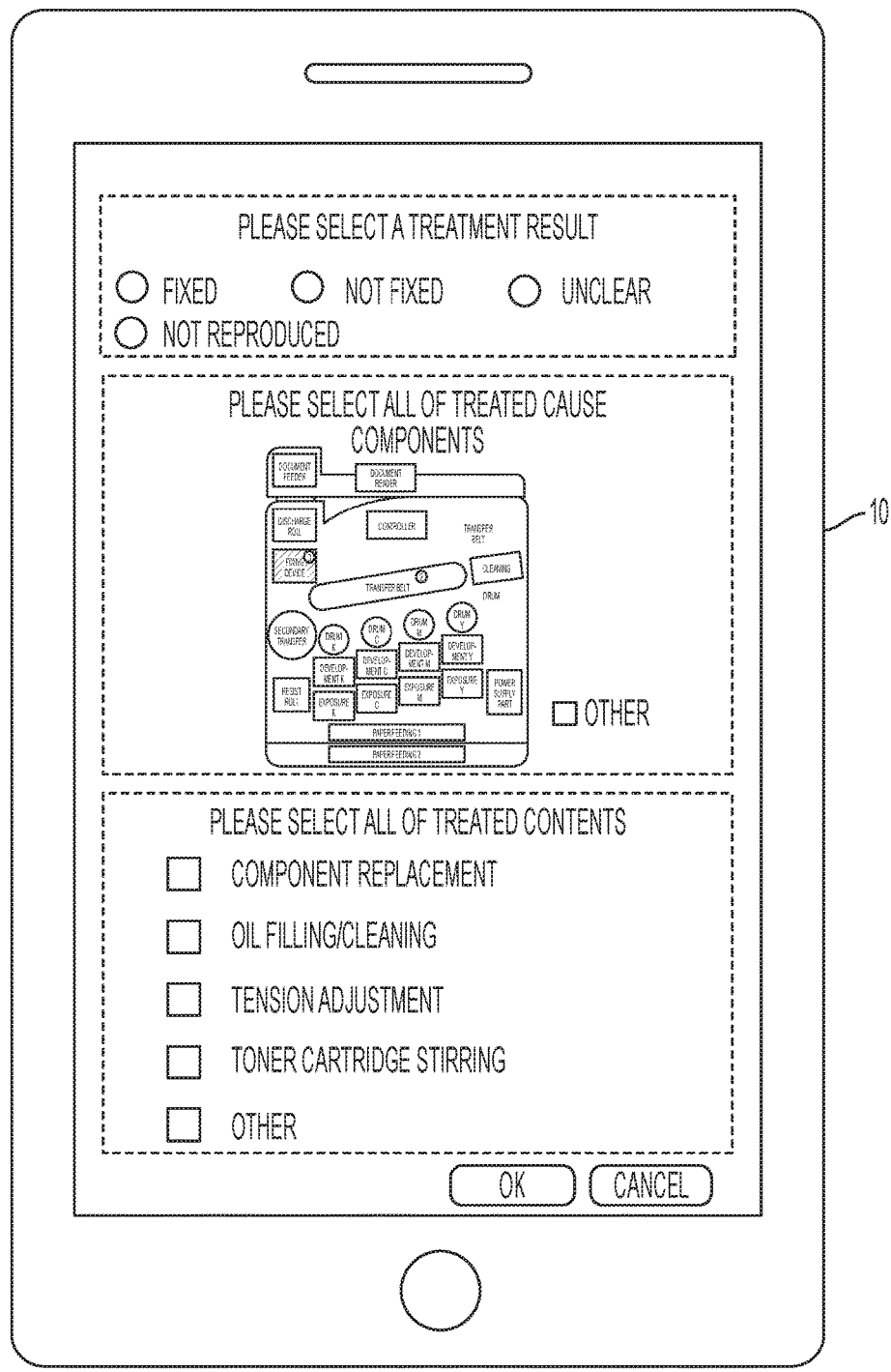
FIG. 17 depicts an example of a display screen that is displayed when receiving an input of a treated component candidate by using a pictorial view of an image forming apparatus 20.

Also, instead of displaying the treated component candidates in a list form, as shown in FIG. 16, a pictorial view of the image forming apparatus 20 may be displayed and an input of the treated component may be received using the pictorial view, as shown in FIG. 17. In the display screen example of FIG. 17, the constitutional components are shown in the pictorial view of the image forming apparatus 20. The respective constitutional components are displayed with priority orders based on the order in which the plural frequency spectrum waveforms received from the server apparatus 50 has been displayed.

Specifically, the photosensitive drum, the transfer belt and the fixing device are numbered to display the priority orders. FIG. 18 is an enlarged view of the selection screen of the treated component candidates in FIG. 17.

In FIG. 18, it can be seen that the photosensitive drum is displayed with a number "1", the transfer belt is displayed with a number "2" and the fixing device is displayed with a number "3". Also, "other" can be selected as the option when the treatment has been executed for a component except the displayed components.

In FIGS. 17 and 18, although the illustration image of the outer appearance of the apparatus has been used, a photograph image of the outer appearance of the apparatus may also be used.

It is ideal to input the treatment situation (to report the treatment result) by the service engineer immediately after executing the treatment for the apparatus. However, even though the service engineer has executed the treatment, the service engineer may not input the executed treatment situation. Therefore, when there is a non-input item in the input items of the treatment situation of the abnormal sound, a popup display may be displayed on the activation screen of the abnormal sound diagnostic device 10 so as to display that there is a non-input item.

Figure 19:
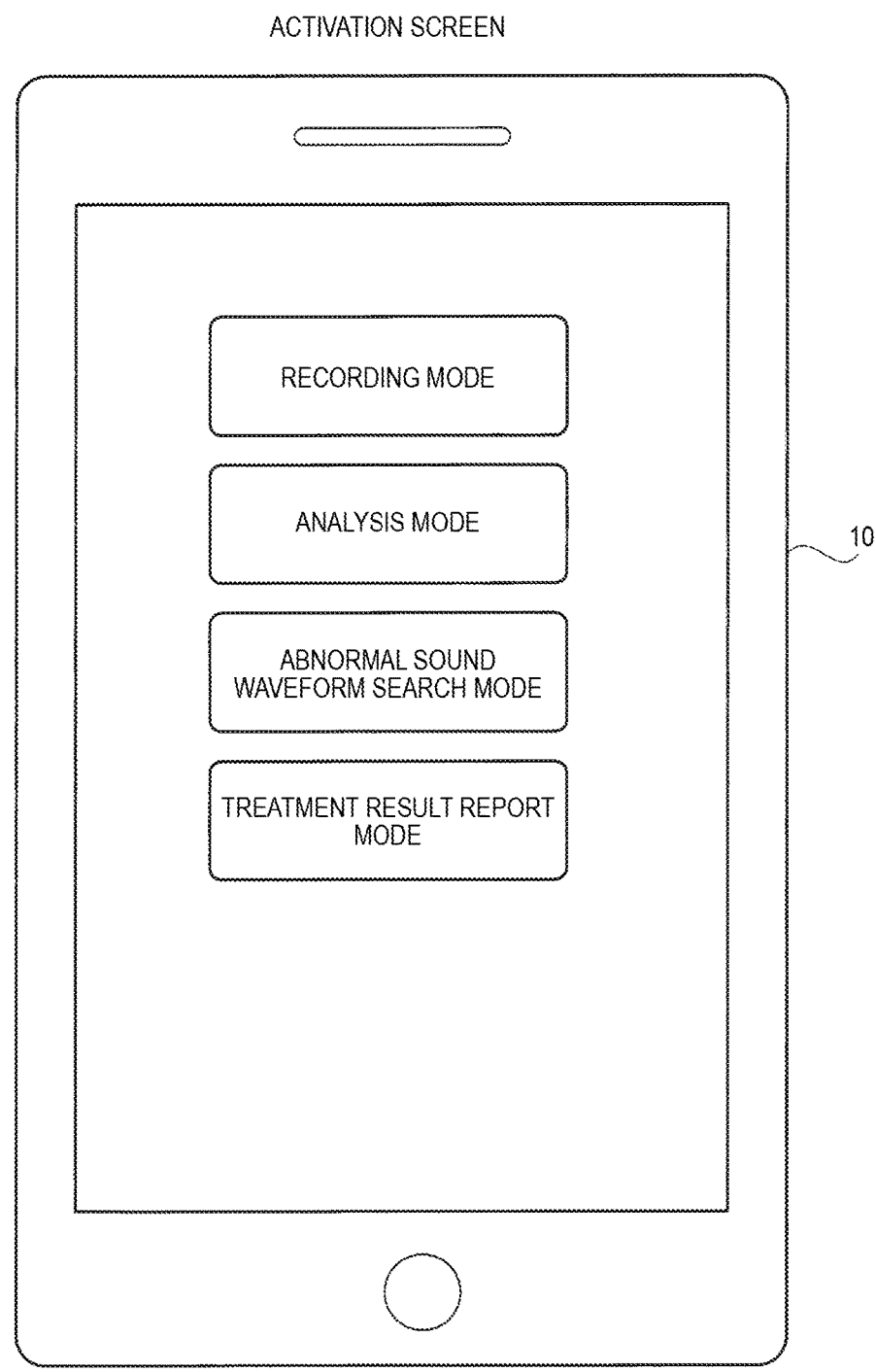
FIG. 19 depicts an example of a usual activation screen of the abnormal sound diagnostic device 10.

For example, a case where a display as shown in FIG. 19 is displayed on a usual activation screen is described. In the activation screen example shown in FIG. 19, selection buttons of a recording mode, an analysis mode, an abnormal sound waveform search mode and a treatment result report mode are displayed.

Figure 20:
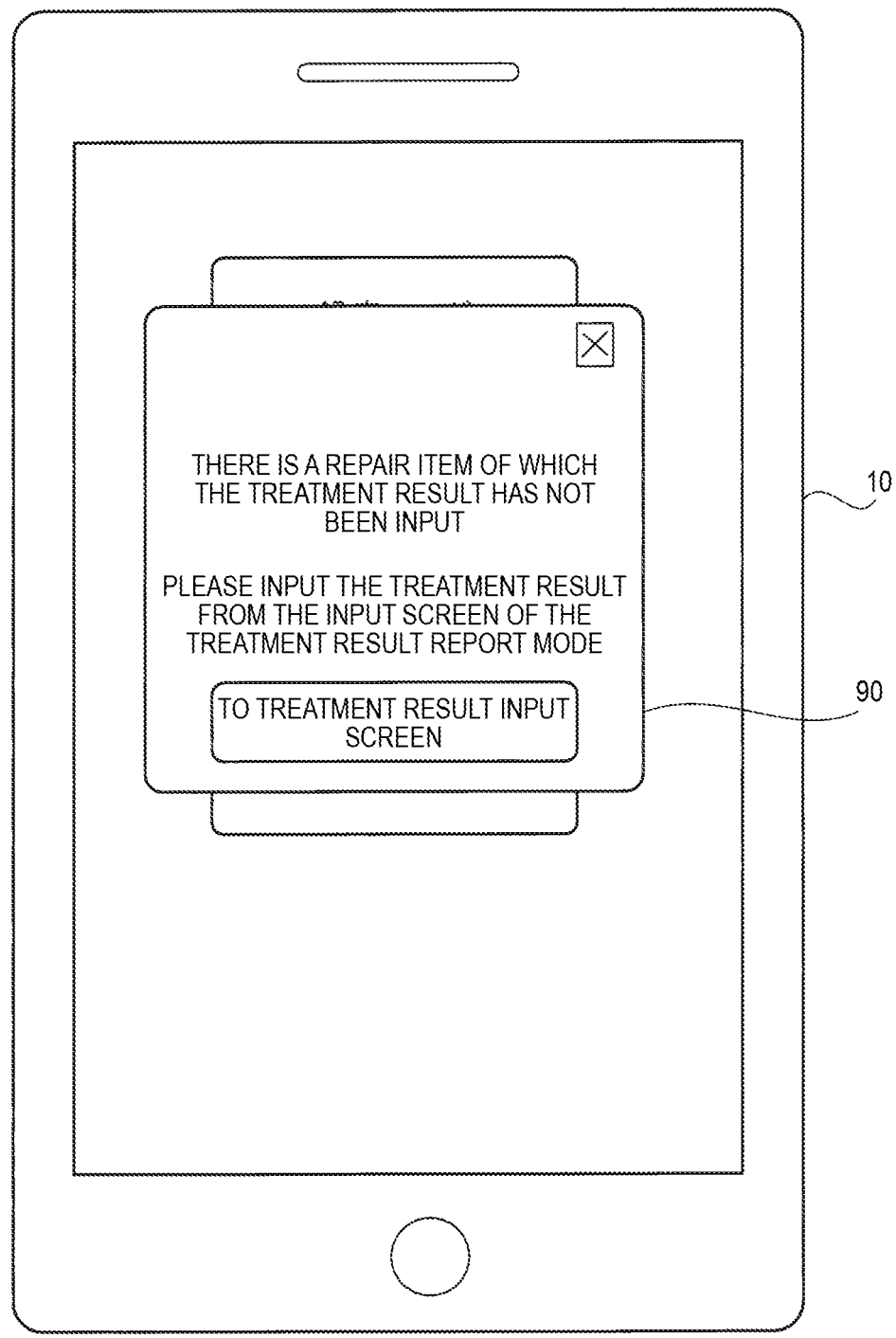
FIG. 20 depicts an example of a screen that is displayed when displaying a popup display 90 on the activation screen so as to urge an input of a treatment result.

However, when there is a non-input item in the input items of the treatment situation of the abnormal sound, for example, a popup display 90 as shown in FIG. 20 may be displayed on the activation screen so as to urge an input of the treatment result.

When a button "To the treatment result input screen" displayed in the popup display 90 is touched, the display is directly shifted to the treatment result input screen as shown in FIG. 15.

In the meantime, a configuration is also possible in which a notification area to a user is provided at an upper side of the display screen without the popup display 90 as shown in FIG. 20 and the information, which indicates that there is a non-input item in the input items of the treatment situation of the abnormal sound, is displayed in the notification area so as to urge an input of the non-input item.

In the display screen example described above, one service engineer executes the treatment for the abnormal sound and inputs the treatment result. However, when there is no component for replacement, the service engineer may not execute the treatment at the site. In this case, since it is necessary to execute the treatment such as component replacement at a later date, a service engineer having analyzed the cause of the abnormal sound and a service engineer who will actually execute the treatment may be different.

Figure 21:
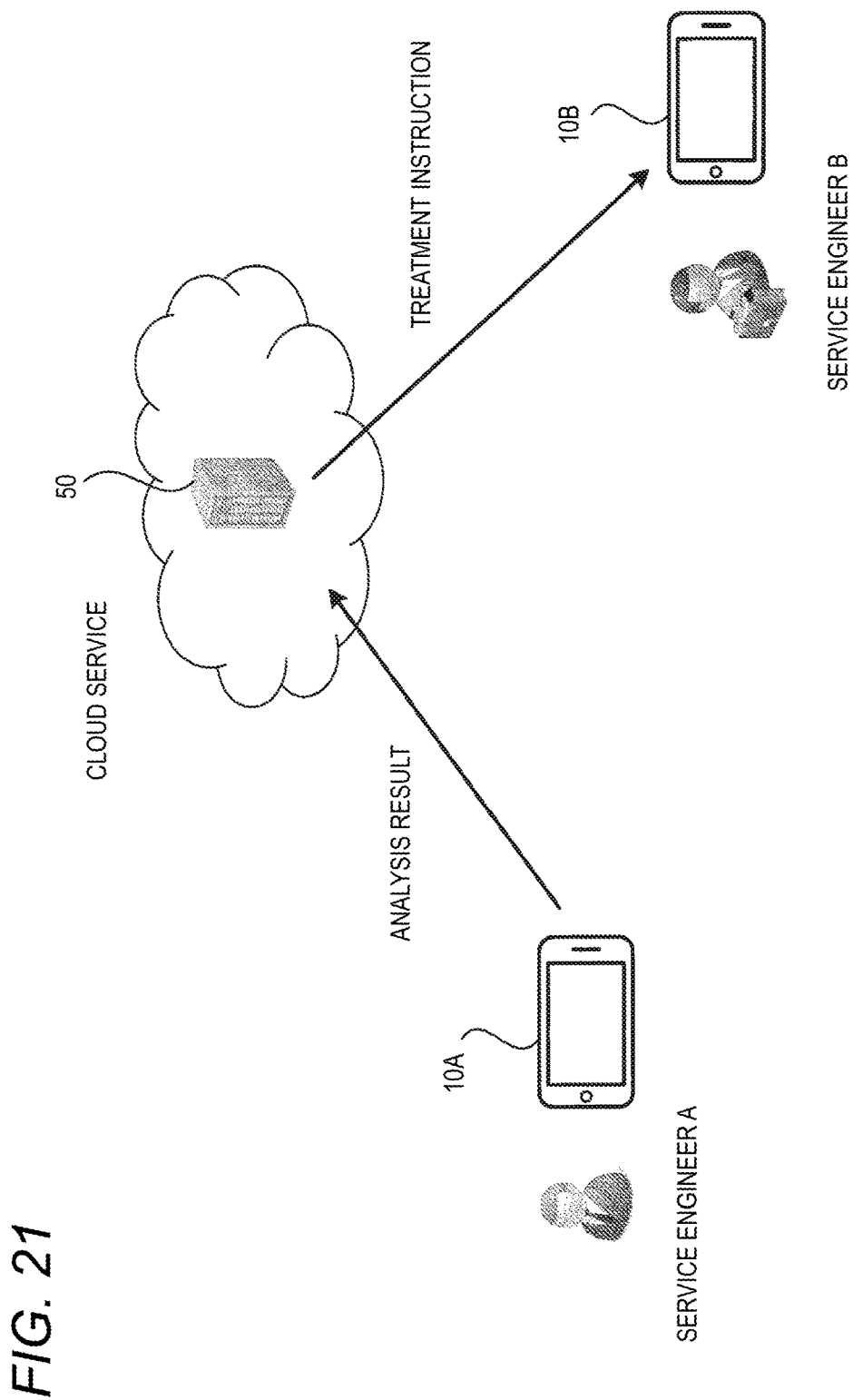
FIG. 21 depicts an aspect where a service engineer A analyzes an abnormal sound cause, reports an analysis result to the server apparatus 50 and the server apparatus instructs an abnormal sound diagnostic device 10B to execute a treatment.

In this case, for example, as shown in FIG. 21, when a service engineer A analyzes the abnormal sound cause to specify the cause of the abnormal sound and reports the analysis result from the abnormal sound diagnostic device 10A to the server apparatus 50, an abnormal sound diagnostic device 10B of another service engineer B may be instructed to execute the treatment. In this case, when the server apparatus 50 receives diagnosis result information of the treatment content to be executed from the abnormal sound diagnostic device 10A, the server apparatus 50 instructs the abnormal sound diagnostic device 10B different from the abnormal sound diagnostic device 10A to execute the treatment content. Then, the service engineer B having received the treatment instruction executes the treatment of the instructed content.

Figure 22:
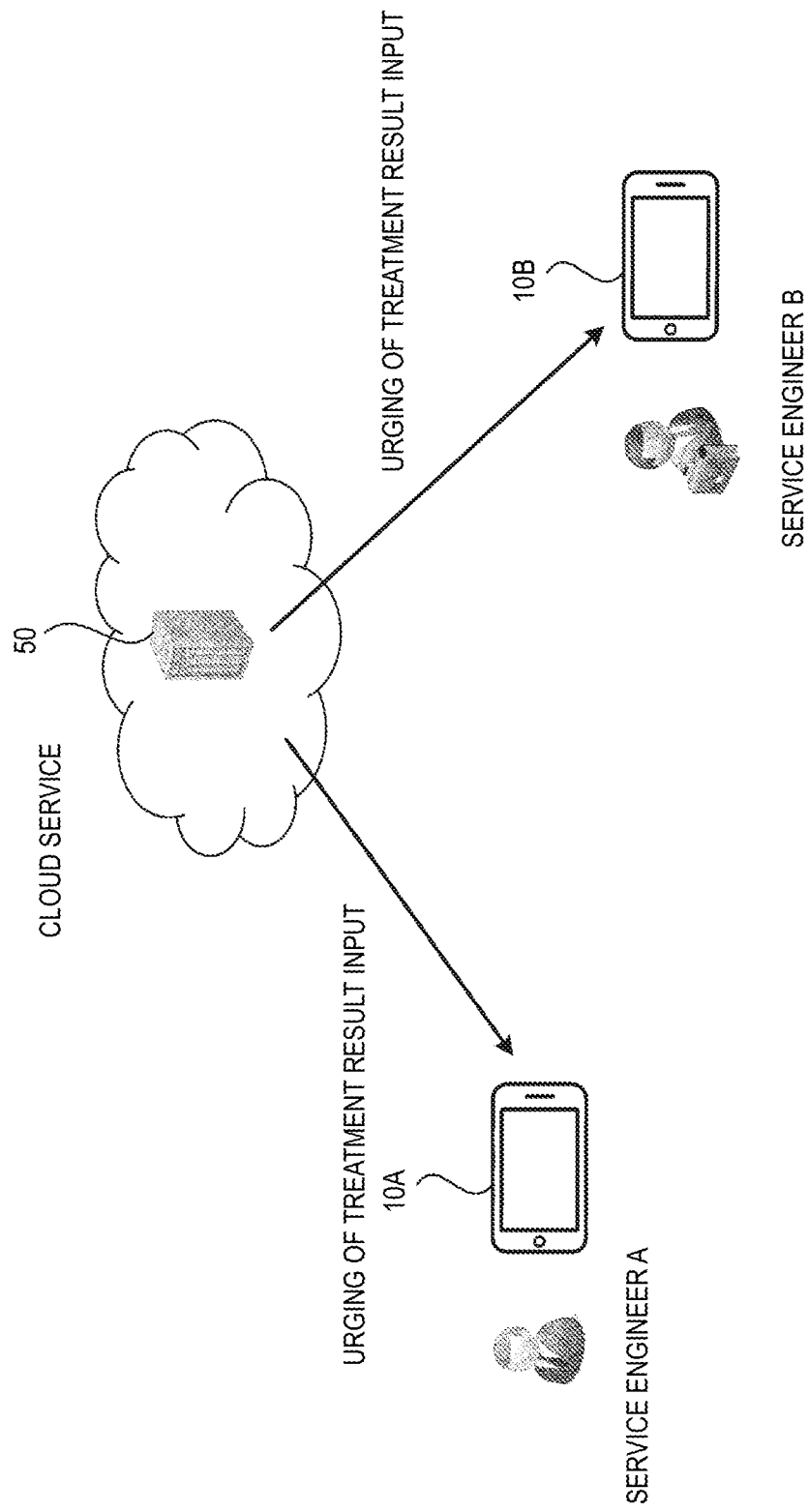
FIG. 22 depicts an aspect where a notification for urging an input of a treatment result is transmitted to both an abnormal sound diagnostic device 10A having transmitted diagnosis result information and the abnormal sound diagnostic device 10B that has been instructed to execute a treatment content.

When there is a non-input item in the input items of the treatment situation of the executed treatment even though the treatment has been executed as described above, the information indicating that there is a non-input item is notified to both the abnormal sound diagnostic device 10A having transmitted the diagnosis result information and the abnormal sound diagnostic device 10B that has been instructed to execute the treatment content so as to urge an input of the treatment result, as shown in FIG. 22. In the meantime, the server apparatus 50 may be configured to notify the information indicating that there is a non-input item to only one of the two abnormal sound diagnostic devices 10A and 10B so as to urge an input of the treatment result.

FIGS. 23 and 24 depict input screen examples, which are displayed when the service engineers A and B urged to input the treatment result input a treatment result, respectively.

In FIG. 23, a case where the service engineer A selects the option of the treatment result "Unclear", the option of the treated component "Fixing device" and the option of the treatment content "Component replacement" by using the abnormal sound diagnostic device 10A is shown. Here, since the service engineer A has not actually executed the treatment, the service engineer A does not perceive whether the abnormal sound has been actually eliminated by the treatment, so that the option "Unclear" is selected as the treatment result.

Also, in FIG. 24, a case where the service engineer B selects the option of the treatment result "Fixed", the option of the treated component "Fixing device", and the option of the treatment content "Component replacement" by using the abnormal sound diagnostic device 10B is shown. Here, since the service engineer B has actually executed the treatment, the service engineer B perceives that the abnormal sound has been actually eliminated by the treatment and the option "Fixed" is selected as the treatment result.

[Modified Embodiments]

The exemplary embodiment has been described using the case where the abnormal sound diagnostic device 10 is a tablet terminal device. However, the present invention is not limited thereto and can also be applied to a case where another device is used as the abnormal sound diagnostic device. For example, the operation panel of the image forming apparatus 20 may be used as the abnormal sound diagnostic device if the operation panel can be detached from a main body and has embedded functions of performing communication with the server apparatus 50 and acquiring the sound signal.

Also, the exemplary embodiment has been described using the case where the abnormal sound diagnostic 10 has the microphone 17 embedded therein. However, when the abnormal sound diagnostic device 10 has a sound recording function, the acquisition unit of the sound signal may be implemented by connecting a sound collection device such as the microphone to an outside.

Also, the exemplary embodiment has been described using the case where the region that is estimated as the abnormal sound is designated by the user's touch operation. However, the present invention is not limited thereto. When the region that is estimated as the abnormal sound is designated by other methods such as a method of directly inputting a frequency that is estimated as the abnormal sound by numbers, which is a case where the region is designated by a pen input, a method of designating the region by a mouse operation, and the like, the present invention can also be applied.

Also, the exemplary embodiment has been described using the case where the target apparatus of the abnormal sound analysis is the image forming apparatus. However, the target apparatus of the abnormal sound analysis is not limited to the image forming apparatus. The present invention can be applied to other apparatus inasmuch as the apparatus may cause the abnormal sound having periodicity.

In the above, the diverse exemplary embodiments have been described. However, the exemplary embodiments may be combined.

Also, the present disclosure is not limited to the exemplary embodiment and can be implemented in diverse forms without departing from the gist of the present disclosure.

What is claimed is:

1. A diagnostic device comprising:
at least one processor configured to execute an acquisition unit that acquires sound information from a target apparatus,
wherein the acquired sound information includes a first abnormal sound; and
a display configured to display a first analysis result obtained by a time-frequency analysis on the acquired sound information,
wherein the display is configured to display a plurality of second analysis results, wherein each one of the second analysis results was obtained by a time-frequency analysis on sound information of another abnormal sound,
wherein the display is configured to display the second analysis results in a descending order of a likelihood of being a cause of the first abnormal sound, and
wherein the display is configured to display treatment candidates on a screen for inputting a treatment situation of the first abnormal sound, based on the order in which the second analysis results have been displayed.

2. A diagnostic device comprising:
at least one processor configured to execute an acquisition unit that acquires sound information from a target apparatus,
wherein the acquired sound information includes a first abnormal sound; and
a display configured to display a first analysis result obtained by a time-frequency analysis on the acquired sound information,
wherein the display is configured to display a plurality of second analysis results, wherein each one of the second analysis results was obtained by a time-frequency analysis on sound information of another abnormal sound,
wherein the display is configured to display the second analysis results in descending order of a likelihood of being a cause of the first abnormal sound, and
wherein the display is configured to display, on a screen for inputting a treatment situation of the first abnormal sound, a pictorial view configured to receive an input of one of treatments with a priority order of each of the treatments based on the order in which the second analysis results have been displayed.

3. The diagnostic device according to claim 1, wherein the at least one processor is further configured to execute:
an analysis unit that performs the time-frequency analysis on the sound information and generates the first analysis result indicative of a temporal change of an intensity distribution for each frequency;
an extraction unit that extracts information of a period and a frequency of the first abnormal sound from the first analysis result;
a communication unit that performs communication with an external apparatus;
a transmission unit that transmits the information of the period and the frequency of the first abnormal sound extracted by the extraction unit to the external apparatus via the communication unit; and
a receiving unit that receives, from the external apparatus via the communication unit, one of the second analysis results corresponding to the first analysis result generated by the analysis unit,
wherein the display is configured to display the first analysis result generated by the analysis unit and the one of the second analysis results received by the receiving unit.

4. The diagnostic device according to claim 2, wherein the at least one processor is further configured to execute:
an analysis unit that performs the time-frequency analysis on the sound information and generates the first analysis result indicative of a temporal change of an intensity distribution for each frequency;
an extraction unit that extracts information of a period and a frequency of the first abnormal sound from the first analysis result;
a communication unit that performs communication with an external apparatus;
a transmission unit that transmits the information of the period and the frequency of the first abnormal sound extracted by the extraction unit to the external apparatus via the communication unit; and
a receiving unit that receives, from the external apparatus via the communication unit, one of, one of the second analysis results corresponding to the first analysis result generated by the analysis unit, wherein the display is configured to display the first analysis result generated by the analysis unit and the one of the second analysis results received by the receiving unit.

5. The diagnostic device according to claim 1, wherein the display is configured to display, on the screen for inputting a treatment situation of the first abnormal sound:
   an option indicating that the first abnormal sound has been eliminated;
   an option indicating that the first abnormal sound has not been eliminated; and
   an option indicating that it is unclear whether the first abnormal sound has been eliminated.

6. The diagnostic device according to claim 2, wherein the display is configured to display, on the screen for inputting a treatment situation of the first abnormal sound:
   an option indicating that the first abnormal sound has been eliminated;
   an option indicating that the first abnormal sound has not been eliminated; and
   an option indicating that it is unclear whether the first abnormal sound has been eliminated.

7. The diagnostic device according to claim 3, wherein the display is configured to display, on the screen for inputting a treatment situation of the first abnormal sound:
   an option indicating that the first abnormal sound has been eliminated;
   an option indicating that the first abnormal sound has not been eliminated; and
   an option indicating that it is unclear whether the first abnormal sound has been eliminated.

8. The diagnostic device according to claim 4, wherein the display is configured to display, on the screen for inputting a treatment situation of the first abnormal sound:
   an option indicating that the first abnormal sound has been eliminated;
   an option indicating that the first abnormal sound has not been eliminated; and
   an option indicating that it is unclear whether the first abnormal sound has been eliminated.

9. The diagnostic device according to claim 1, wherein the display is configured to, in response to there being an item of the treatment situation of the first abnormal sound which has not been input, display information indicating that there is the item which has not been input.

10. The diagnostic device according to claim 2, wherein the display is configured to, in response to there being an item of the treatment situation of the first abnormal sound which has not been input, display information indicating that there is the item which has not been input.

11. The diagnostic device according to claim 3, wherein the display is configured to, in response to there being an item of the treatment situation of the first abnormal sound which has not been input, display information indicating that there is the item which has not been input.

12. The diagnostic device according to claim 4, wherein the display is configured to, in response to there being an item of the treatment situation of the first abnormal sound which has not been input, display information indicating that there is the item which has not been input.

13. The diagnostic device according to claim 1, wherein input items of the treatment situation of the first abnormal sound comprise an item of a treatment result and an item of a treatment content.

14. The diagnostic device according to claim 2, wherein input items of the treatment situation of the first abnormal sound comprise an item of a treatment result and an item of a treatment content.

15. The diagnostic device according to claim 3, wherein input items of the treatment situation of the first abnormal sound comprise an item of a treatment result and an item of a treatment content.

16. The diagnostic device according to claim 4, wherein input items of the treatment situation of the first abnormal sound comprise an item of a treatment result and an item of a treatment content.

17. A diagnostic method comprising:
   acquiring sound information from a target apparatus,
      wherein the acquired sound information includes a first abnormal sound;
   displaying:
      a first analysis result obtained by a time-frequency analysis on the acquired sound information; and
      a plurality of second analysis results, wherein each one of the second analysis results was obtained by a time-frequency analysis on sound information of another abnormal sound,
   displaying the second analysis results in descending order of a likelihood of being a cause of the first abnormal sound; and
   displaying treatment candidates on a screen for inputting a treatment situation of the first abnormal sound, based on the order in which the second analysis results have been displayed.

18. The diagnostic device according to claim 1, wherein the display is configured to display each one of the second analysis results at a same time in the descending order of the likelihood of being the cause of the first abnormal sound.

19. The diagnostic device according to claim 1, wherein the another abnormal sound was generated before the first abnormal sound by a second apparatus similar to the target apparatus.

* * * * *